US007175831B2

(12) United States Patent
Achilefu et al.

(10) Patent No.: US 7,175,831 B2
(45) Date of Patent: Feb. 13, 2007

(54) LIGHT SENSITIVE COMPOUNDS FOR INSTANT DETERMINATION OF ORGAN FUNCTION

(75) Inventors: Samuel Achilefu, St. Louis, MO (US); Raghavan Rajagopalan, Solon, OH (US); Richard B. Dorshow, St. Louis, MO (US); Joseph E. Bugaj, St. Charles, MO (US); Hermo N. Jimenez, Hazelwood, MO (US); Muthunadar P. Periasamy, Chesterfield, MO (US)

(73) Assignee: Mallinckrodt, Inc., St. Louis, MO (US)

( * ) Notice: Subject to any disclaimer, the term of this patent is extended or adjusted under 35 U.S.C. 154(b) by 289 days.

(21) Appl. No.: 10/751,232

(22) Filed: Jan. 2, 2004
(Under 37 CFR 1.47)

(65) Prior Publication Data
US 2004/0213740 A1    Oct. 28, 2004

Related U.S. Application Data

(63) Continuation-in-part of application No. 09/688,942, filed on Oct. 16, 2000, now Pat. No. 6,673,334.

(51) Int. Cl.
*A61B 10/00* (2006.01)
*A61B 5/00* (2006.01)
*A61B 8/00* (2006.01)

(52) U.S. Cl. ............... 424/9.6; 424/1.11; 424/1.65; 424/9.1; 514/373

(58) Field of Classification Search ............. 424/1.11, 424/1.65, 1.69, 9.1, 9.2, 9.3, 9.4, 9.5, 9.6, 424/9.7, 9.8, 1.49, 520; 530/300, 350, 387, 530/322, 399; 548/146; 534/7, 10–16; 536/1.11; 435/1.11, 325; 514/359, 369, 370, 372, 430, 514/373
See application file for complete search history.

(56) References Cited

U.S. PATENT DOCUMENTS

| 4,574,124 | A | 3/1986 | Kabbe et al. ............... 514/228 |
|---|---|---|---|
| 5,106,990 | A | 4/1992 | Ohno et al. ................. 548/427 |
| 5,346,801 | A | 9/1994 | Watanabe et al. ........... 430/253 |
| 5,395,619 | A | 3/1995 | Zalipsky .................... 424/450 |
| 5,492,814 | A | 2/1996 | Weissleder ................. 435/725 |
| 5,496,689 | A | 3/1996 | Ogawa ....................... 430/505 |
| 5,631,018 | A | 5/1997 | Zalipsky et al. ............ 424/450 |
| 5,840,023 | A | 11/1998 | Oraevsky et al. ........... 600/407 |
| 5,968,479 | A | 10/1999 | Ito et al. |
| 5,977,538 | A | 11/1999 | Unger et al. ............. 250/227.2 |
| 6,083,485 | A | 7/2000 | Licha et al. ................ 434/9.6 |
| 6,083,486 | A | 7/2000 | Licha et al. |
| 6,150,405 | A | 11/2000 | Proctor ...................... 514/474 |
| 6,180,085 | B1 | 1/2001 | Achilefu et al. ............ 424/9.6 |
| 6,180,086 | B1 | 1/2001 | Achilefu et al. ............ 424/9.6 |
| 6,180,087 | B1 | 1/2001 | Achilefu et al. ............ 424/9.6 |
| 6,183,726 | B1 | 2/2001 | Achilefu et al. ............ 424/9.6 |
| 6,190,641 | B1 | 2/2001 | Achilefu et al. ............ 424/9.6 |
| 6,217,848 | B1 | 4/2001 | Achilefu et al. ............ 424/9.1 |
| 6,258,340 | B1 | 7/2001 | Licha et al. ................ 424/9.6 |
| 6,258,378 | B1 | 7/2001 | Schneider et al. .......... 424/450 |
| 6,264,919 | B1 | 7/2001 | Achilefu et al. ............ 424/9.6 |
| 6,277,403 | B1 | 8/2001 | Perez Mendez et al. .... 424/450 |
| 6,329,531 | B1 | 12/2001 | Turner et al. |
| 6,395,257 | B1 | 5/2002 | Achilefu et al. ............ 424/9.6 |
| 6,406,713 | B1 | 6/2002 | Janoff et al. ................ 424/450 |
| 6,534,041 | B1 | 3/2003 | Licha et al. |
| 6,610,322 | B1 | 8/2003 | Keller et al. ................ 424/450 |
| 6,673,334 | B1 * | 1/2004 | Achilefu et al. ............ 424/9.6 |

FOREIGN PATENT DOCUMENTS

WO    WO 96/00902    1/1996

OTHER PUBLICATIONS

PCT, *International Search Report*, Date Mailed Feb. 13, 2002 (1 page).
Christopher C. Baker, M.D., *Epidemiology of Trauma Deaths*, Amer. Jour. of Surg., vol. 150, 1980, pp. 144-150.
John Baldas et al, *Preparation, HPLC Studies and Biological Behaviour of 99mTc- and 99mTcN-radiopharmaceuticals Based on Quinoline Type Ligands*, Nucl. Med. Biol., vol. 19, No. 4, 1992, pp. 491-496.
Braun-Falco et al., *Liposome Dermatics*, Greisbach Conference, Springer-Verlag, 1992, pp. 69-117.
Frank B. Cerra, M.D., *Multiple Organ Failure Syndrome*, New Horizons: Multiple Organ Failure, Society of Critical Care Medicine, 1989, pp. 1-24.
Peter L. Choyke et al., *Hydrated clearance of gadolinium-DTPA as a measurement of glomerular filtration rate*, Kidney International, vol. 41, 1992, pp. 1595-1598.

(Continued)

*Primary Examiner*—Dameron L. Jones
(74) *Attorney, Agent, or Firm*—Wood, Herron, & Evans LLP

(57) ABSTRACT

Highly hydrophilic indole and benzoindole derivatives that absorb and fluoresce in the visible region of light are disclosed. These compounds are useful for physiological and organ function monitoring. Particularly, the molecules of the invention are useful for optical diagnosis of renal and cardiac diseases and for estimation of blood volume in vivo.

25 Claims, 11 Drawing Sheets

OTHER PUBLICATIONS

Cdr. P.D. Doolan, MC, USN, et al., *A Clinical Appraisal of the Plasma Concentration and Endogenous Clearance of Creatinine*, Amer. Jour. of Med., vol. 32, 1962, pp. 65-79.

Richard B. Dorshow et al., *Monitoring physiological function by detection of exogenous flurosecent contrast agents*, Optical Diagnostics of Biological Fludis IV, A. Priezzhev and T. Asakura, Eds., Procedings of SPIE, 1999, vol. 3599, pp. 2-8.

Dorshow et al., *Optical Detection of Hepatic and Renal Function*, Bull. Am. Phys. Soc., vol. 42, No. 1, (1997) p. 681.

Richard B. Dorshow et al., *Noninvasive Fluorescence Detection of Hepatic and Renal Function*, Journal of Biomedical Optics, vol. 3, No. 3, 1998, pp. 340-345.

James H. Flanagan, Jr., et al., *Near-Infrared Heavy-Atom-Modified Fluorescent Dyes for Base-Calling in DNA-Sequencing Applications Using Temporal Discrimination*, Anal. Chem., vol. 70, No. 13, 1998, pp. 2676-2684.

P. Guesry et al., *Measurement of glomerular filtration rate by fluorescent excitation of non-radioactive meglumine iothalamate*, Clincal Nephrology, vol. 3, No. 4, 1975, pp. 134-138.

L.Hansen et al., *Synthesis of the Sulphonate and Phosphonate Derivatives of Mercaptoacetyltriglycine, X-Ray Crystal Structure of Ha2[ReO(Mercaptoacetylglycylglycyl'Aminomethanesulphonate)]-3H2O*, Metal-Based Drugs, vol. 1, No. 1, 1993, 31-39.

Lasic & Martin , Eds., *Stealth Liposomes*, CRC Press, 1995, pp. 1-6, 13-62, 93-147, 197-209, 233-244.

Richard Lewis et al., *Comparative Evaluation of Urographic Contrast Media, Inulin, and 99mTc-DTPA Clearance Methods for Determination of Clomerular Filtration Rate in Clinical Transplantation*, Transplantation, vol. 48, No. 5, 1989, pp. 790-796.

S. Lundqvist et al., *Iohexol Clearance for Renal Function Measurement in Gynaecologic Cancer Patients*, Acta Radiologica, vol. 37, 1996, pp. 582-586.

Joanna Malicka, et al., *Metal-enhanced emission from indocyanine green: a new approach to in vivo imaging*, Journal of Biomedical Optics, vol. 8, No. 3, Jul. 2003, pp. 472-478.

G. Muller et al. (ed.), *Medical Optical Tomography, Functional Imaging and Monitoring*, SPIE Optical Engineering Press, The International Society of Optical Engineering, Bellingham, WA 1993.

Roland Muller-Suur et al., *Glomerular Filtration and Tubular Secretion of MAG-3 in the Rat Kidney*, The Journal of Nuclear Medicine, vol. 30, 1989, pp. 1986-1991.

Dennis L. Nosco et al., *Chemistry of technetium radiopharmaceuticals 1: Chemistry behind the development of technetium-99m compounds to determine kidney function*, Coordination Chemistry Reviews, vol. 184, 1999, pp. 91-123.

Carlos A. Rabito et al., *Renal Function in Patients at Risk of Contrast Material-induced Acute Renal Failure: Noninvasive, Real-Time Monitoring*, Radiology, vol. 186, No. 3, 1993, pp. 851-854.

G. Regel, M.D., et al., *Treatment Results of Patients with Multiple Trauma: An Analysis of 3406 Cases Treated between 1972 and 1991 at a German Level 1 Trauma Center*, The Journal of Trauma, vol. 38, No. 1, 1995, pp. 70-77.

G.A. Reynolds et al., *Stable Heptamethine Pyrylium Dyes That Absorb in the Infrared*, J. Org. Chem., vol. 42, No. 5, 1977, pp. 885-888.

Francoise Roch-Ramel et al., *Renal excretion and tubular transport of organic anions and cations*, Oxford University Press, N.Y., Handbook of Physiology, Sec. 8, Neurological Physiology, vol. II, E.E. Windhager, Ed., 1992, pp. 2189-2262.

Morgan Sohtell et al., *FITC-inulin as a kidney tubule marker in the rat*, Acta Physiol. Scand., vol. 119, 1983, pp. 313-316.

P.L. Southwick et al., *"One Pot" Fischer Synthesis of (2, 3, 3-Trimethyl-3-H-Indol-5-yl)-Acetic Acid, Derivatives as Intermediates for Fluorescent Biolabels*, Org. Prep. Proced. Int. Briefs, vol. 20, No. 3, 1988, 279-284.

W. Newlon Tauxe , *Tubular Function*, Nuclear Medicine in Clinical Urology and Nephrology, Appleton-Century-Crofts, Prentice-Hall, Inc., 1985, pp. 77-105.

Nicholas L. Tilney, M.D., *Acute Renal Failure in Surgical Patients, Causes, Clinical Patterns, and Care*, Surgical Clinics of North America, vol. 63, No. 2, 1983, pp. 357-377.

Michael F. Tweedle, Ph.D. et al., *A Noninvasive Method for Monitoring Renal Status at Bedside*, Investigative Radiology, vol. 32, No. 12, 1997, pp. 802-805.

Bruce E. VanZee, M.D. et al., *Renal Injury Associated with Intravenous Pyelography in Nondiabetic and Diabetic Patients*, Annals of Internal Medicine, vol. 89, 1978, pp. 51-54.

* cited by examiner

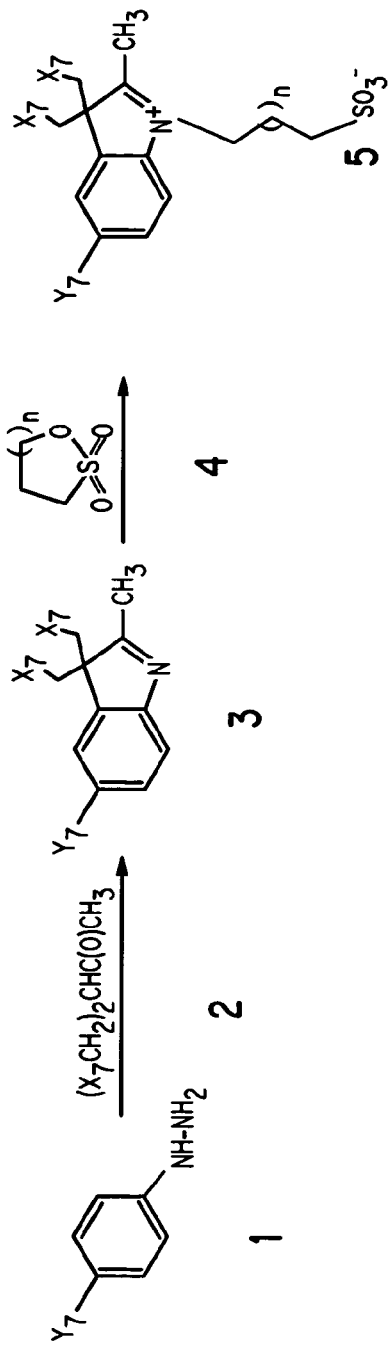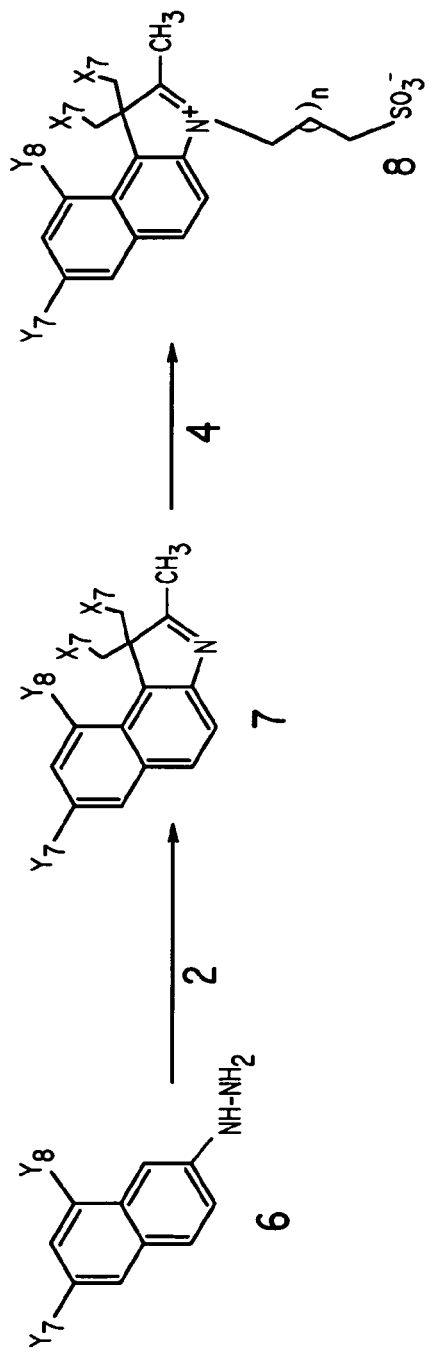
FIG. 1 : n = 1–3; $X_7 = H, OH$; $Y_7 = H, SO_3^-, CO_2H, CH_2CO_2H, CH_2OH$
FIG. 2 : n = 1–3; $X_7 = H, OH$; $Y_7, Y_8 = H, SO_3^-, CO_2H, CH_2CO_2H, CH_2OH$ n = 1-3; $X_7$ = H, OH; $Y_7$ = H, $SO_3^-$, $CO_2H$, $CH_2CO_2H$, $CH_2OH$; $R_f$ = $(CH_3)_2N$ or OH; $R_g$ = $(CH_3)_2N^+$ or CHO n = 1-3; X7 = H, OH; Y7 = H, SO3−, CO2H, CH2CO2H, CH2OH; Rf = (CH3)2N or OH; Rg = (CH3)2N+ or CHO n = 1-3; X7 = H, OH; Y7 = H, SO3⁻, CO2H, CH2CO2H, CH2OH n = 1-3; $X_7$ = H, OH; $Y_7$, $Y_8$ = H, $SO_3^-$, $CO_2H$, $CH_2CO_2H$, $CH_2OH$ n = 1-3; $X_7$ = H, OH; $Y_7$, $Y_8$ = H, $SO_3^-$, $CO_2H$, $CH_2CO_2H$, $CH_2OH$

LIGHT SENSITIVE COMPOUNDS FOR INSTANT DETERMINATION OF ORGAN FUNCTION

This application is a Continuation-In-Part of U.S. patent application Ser. No. 09/688,942 filed Oct. 16, 2000, now U.S. Pat. No. 6,673,334 and expressly incorporated by reference herein in its entirety.

FIELD OF THE INVENTION

This invention relates to novel optical probes for use in physiological function monitoring, particularly indole and benzoindole compounds.

BACKGROUND OF THE INVENTION

Dynamic monitoring of physiological functions of patients at the bedside is highly desirable in order to minimize the risk of acute renal failure brought about by various clinical, physiological, and pathological conditions (C. A. Rabito, L. S. T. Fang, and A. C. Waltman, *Renal function in patients at risk with contrast material-induced acute renal failure: Noninvasive real-time monitoring, Radiology* 1993, 186, 851–854; N. L. Tilney, and J. M. Lazarus, *Acute renal failure in surgical patients: Causes, clinical patterns, and care, Surgical Clinics of North America,* 1983, 63, 357–377; B. E. VanZee, W. E. Hoy, and J. R. Jaenike, *Renal injury associated with intravenous pyelography in non-diabetic and diabetic patients, Annals of Internal Medicine,* 1978, 89, 51–54; S. Lundqvist, G. Edbom, S. Groth, U. Stendahl, and S. O. Hietala, *Iohexol clearance for renal function measurement in gynecologic cancer patients, Acta Radiologica,* 1996, 37, 582–586; P. Guesry, L. Kaufman, S. Orlof, J. A. Nelson, S. Swann, and M. Holliday Measurement of glomerular filtration rate by fluorescent excitation of non-radioactive meglumine iothalamate, Clinical Nephrology,* 1975, 3, 134–138). This monitoring is particularly important in the case of critically ill or injured patients because a large percentage of these patients face the risk of multiple organ failure (MOF), resulting in death (C. C. Baker et al., *Epidemiology of Trauma Deaths, American Journal of Surgery,* 1980, 144–150; G. Regel et al., *Treatment Results of Patients with Multiple Trauma: An Analysis of* 3406 *Cases Treated Between 1972 and 1991 at a German Level I Trauma Center, Journal of Trauma,* 1995, 38, 70–77). MOF is a sequential failure of lung, liver, and kidneys, and is incited by one or more severe causes such as acute lung injury (ALI), adult respiratory distress syndrome (ARDS), hypermetabolism, hypotension, persistent inflammatory focus, or sepsis syndrome. The common histological features of hypotension and shock leading to MOF include tissue necrosis, vascular congestion, interstitial and cellular edema, hemorrhage, and microthrombi. These changes affect the lung, liver, kidneys, intestine, adrenal glands, brain, and pancreas, in descending order of frequency (J. Coalson, Pathology of Sepsis, Septic Shock, and Multiple Organ Failure, *New Horizons: Multiple Organ Failure Syndrome,* D. J. Bihari and F. B. Cerra (Eds.), *Society of Critical Care Medicine,* Fullerton, Calif., 1986, pp. 27–59). The transition from early stages of trauma to clinical MOF is marked by the extent of liver and renal failure and a change in mortality risk from about 30% to about 50% (F. B. Cerra, Multiple Organ Failure Syndrome. *New Horizons: Multiple Organ Failure,* D. J. Bihari and F. B. Cerra (Eds). *Society of Critical Care Medicine,* Fullerton, Calif., 1989, pp. 1–24).

Serum creatinine measured at frequent intervals by clinical laboratories is currently the most common way of assessing renal function and following the dynamic changes in renal function which occur in critically ill patients (P. D. Doolan, E. L. Alpen, and G. B. Theil, A clinical appraisal of the plasma concentration and endogenous clearance of creatinine, American Journal of Medicine, 1962, 32, 65–79; J. B. Henry (Ed). *Clinical Diagnosis and Management by Laboratory Methods.* 17*th Edition,* W. B. Saunders, Philadelphia, Pa., 1984); C. E. Speicher, *The right test: A physician's guide to laboratory medicine,* W. B. Saunders, Philadelphia, Pa., 1989). These values are frequently misleading, since age, state of hydration, renal perfusion, muscle mass, dietary intake, and many other clinical and anthropometric variables affect the value. In addition, a single value returned several hours after sampling is difficult to correlate with other important physiologic events such as blood pressure, cardiac output, state of hydration and other specific clinical events (e.g., hemorrhage, bacteremia, ventilator settings and others). An approximation of glomerular filtration rate can be made via a 24-hour urine collection, but this requires 24 hours to collect the sample, several more hours to analyze the sample, and a meticulous bedside collection technique. New or repeat data are equally cumbersome to obtain. Occasionally, changes in serum creatinine must be further adjusted based on the values for urinary electrolytes, osmolality, and derived calculations such as the "renal failure index" or the "fractional excretion of sodium." These require additional samples of serum collected contemporaneously with urine samples and, after a delay, precise calculations. Frequently, dosing of medication is adjusted for renal function and thus can be equally as inaccurate, equally delayed, and as difficult to reassess as the values upon which they are based. Finally, clinical decisions in the critically ill population are often as important in their timing as they are in their accuracy.

Exogenous markers such as inulin, iohexol, $^{51}$Cr-EDTA, Gd-DTPA, or $^{99m}$Tc-DTPA have been reported to measure the glomerular filtration rate (GFR) (P. L. Choyke, H. A. Austin, and J. A. Frank, *Hydrated clearance of gadolinium-DTPA as a measurement of glomerular filtration rate, Kidney International,* 1992, 41, 1595–1598; M. F. Tweedle, X. Zhang, M. Fernandez, P. Wedeking, A. D. Nunn, and H. W. Strauss, *A noninvasive method for monitoring renal status at bedside, Invest. Radiol.,* 1997, 32, 802–805; N. Lewis, R. Kerr, and C. Van Buren, *Comparative evaluation of urographic contrast media, inulin, and* $^{99m}$*Tc-DTPA clearance methods for determination of glomerular filtration rate in clinical transplantation, Transplantation,* 1989, 48, 790–796). Other markers such as $^{123}$I and $^{125}$I labeled o-iodohippurate or $^{99m}$Tc-MAG$_3$ are used to assess tubular secretion process (W. N. Tauxe, *Tubular Function,* in *Nuclear Medicine in Clinical Urology and Nephrology,* W. N. Tauxe and E. V. Dubovsky, Editors, pp. 77–105, Appleton Century Crofts, East Norwalk, 1985; R. Muller-Suur, and C. Muller-Suur, *Glomerular filtration and tubular secretion of MAG$_3$ in rat kidney, Journal of Nuclear Medicine,* 1989, 30, 1986–1991). However, these markers have several undesirable properties such as the use of radioactivity or ex-vivo handling of blood and urine samples. Thus, in order to assess the status and to follow the progress of renal disease, there is a considerable interest in developing a simple, safe, accurate, and continuous method for determining renal function, preferably by non-radioactive procedures. Other organs and physiological functions that would benefit from real-time monitoring include the heart, the liver, and blood perfusion, especially in organ transplant patients.

Hydrophilic, anionic substances are generally recognized to be excreted by the kidneys (F. Roch-Ramel, K. Besseghir, and H. Murer, *Renal excretion and tubular transport of organic anions and cations*, Handbook of Physiology, Section 8, *Neurological Physiology*, Vol. II, E. E. Windhager, Editor, pp. 2189–2262, Oxford University Press, New York, 1992; D. L. Nosco, and J. A. Beaty-Nosco, *Chemistry of technetium radiopharmaceuticals 1: Chemistry behind the development of technetium-$^{99m}$ compounds to determine kidney function*, Coordination Chemistry Reviews, 1999, 184, 91–123). It is further recognized that drugs bearing sulfonate residues exhibit improved clearance through the kidneys (J. Baldas, J. Bonnyman, *Preparation, HPLC studies and biological behavior of techentium-$^{99m}$ and $99^{m}TcN0$-radiopharmaceuticals based on quinoline type ligands*, Nuc. Med. Biol., 1999, 19, 491–496; L. Hansen, A. Taylor, L., L. G. Marzilli, *Synthesis of the sulfonate and phosphonate derivatives of mercaptoacetyltriglycine. X-ray crystal structure of $Na_2[ReO(mercaptoacetylglycylglycylaminomethane-sulfonate)]3H_2O$*, Met.-Based Drugs, 1994, 1, 31–39).

Assessment of renal function by continuously monitoring the blood clearance of exogenous optical markers, viz., fluorescein bioconjugates derived from anionic polypeptides, has been developed by us and by others (R. B. Dorshow, J. E. Bugaj, B. D. Burleigh, J. R. Duncan, M. A. Johnson, and W. B. Jones, *Noninvasive fluorescence detection of hepatic and renal function*, Journal of Biomedical Optics, 1998, 3, 340–345; M. Sohtell et al., FITC-Inulin as a Kidney Tubule Marker in the Rat, *Acta. Physiol. Scand.*, 1983, 119, 313–316, each of which is expressly incorporated herein by reference). The main drawback of high molecular weight polypeptides is that they are immunogenic. In addition, large polymers with narrow molecular weight distribution are difficult to prepare, especially in large quantities. Thus, there is a need in the art to develop low molecular weight compounds that absorb and/or emit light that can be used for assessing renal, hepatic, cardiac and other organ functions.

SUMMARY OF THE INVENTION

The present invention overcomes these difficulties by incorporating hydrophilic anionic or polyhydroxy residues in the form of sulfates, sulfonates, sulfamates, phosphates, polyethers, polyamino carboxylic acids and their derivatives, and strategically positioned hydroxyl groups. Thus, the present invention is related to novel dyes containing multiple hydrophilic moieties and their use as diagnostic agents for assessing organ function and functional status of tumors.

The novel compounds of the present invention comprise dyes of Formulas 1 to 6 which are hydrophilic and absorb light in the visible and near infrared regions of the electromagnetic spectrum. The blood clearance rate can be modified by formulating the dyes in liposomes, micelles, or other microparticles. This enhances their use for physiological monitoring of many organs. The ease of modifying the clearance pathways of the dyes after in vivo administration permits their use for physiological monitoring. Compounds with longer blood persistence are useful for angiography and organ perfusion analysis, which is particularly useful in organ transplant and critical ill patients. Predominant kidney clearance of the dyes enables their use for dynamic renal function monitoring, and rapid liver uptake of the dyes from blood serves as a useful index for the evaluation of hepatic function.

As illustrated in FIGS. 1–7, these dyes are designed to inhibit aggregation in solution by preventing intramolecular and intermolecular induced hydrophobic interactions.

The present invention relates particularly to the novel compounds comprising indoles of the general Formula 1

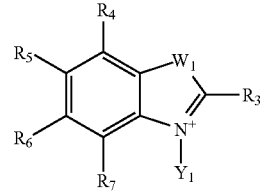

Formula 1 wherein $R_3$, R4, $R_5$, $R_6$, and $R_7$, and $Y_1$ are independently selected from the group consisting of —H, C1–C10 alkoxyl, C1–C10 polyalkoxyalkyl, C1–C20 polyhydroxyalkyl, C5–C20 polyhydroxyaryl, glucose derivatives of R groups, saccharides, amino, C1–C10 aminoalkyl, cyano, nitro, halogen, hydrophilic peptides, arylpolysulfonates, C1–C10 alkyl, C1–C10 aryl, —$SO_3T$, —$CO_2T$, —OH, —$(CH_2)_a SO_3T$, —$(CH_2)_a OSO_3T$, —$(CH_2)_a NHSO_3T$, —$(CH_2)_a CO_2 (CH_2)_b SO_3T$, —$(CH_2)_a OCO(CH_2)_b SO_3T$, —$(CH_2)_a CONH (CH_2)_b SO_3T$, —$(CH_2)_a NHCO(CH_2)_b SO_3T$, —$(CH_2)_a NH-CONH(CH_2)_b SO_3T$, —$(CH_2)_a NHCSNH(CH_2)_b SO_3T$, —$(CH_2)_a OCONH(CH_2)_b SO_3T$, —$(CH_2)_a PO_3 HT$ —$(CH_2)_a PO_3 T_2$, —$(CH_2)_a OPO_3 HT$, —$(CH_2)_a OPO_3 T_2$, —$(CH_2)_a NHPO_3 HT$, —$(CH_2)_a NHPO_3 T_2$, —$(CH_2)_a CO_2(CH_2)_b PO_3 HT$, —$(CH_2)_a CO_2(CH_2)_b PO_3 T_2$, —$(CH_2)_a OCO(CH_2)_b PO_3 HT$, —$(CH_2)_a OCO(CH_2)_b PO_3 T_2$, —$(CH_2)_a CONH (CH_2)_b PO_3 HT$, —$(CH_2)_a CONH(CH_2)_b PO_3 T_2$, —$(CH_2)_a NHCO(CH_2)_b PO_3 HT$, —$(CH_2)_a NHCO(CH_2)_b PO_3 T_2$, —$(CH_2)_a NHCONH(CH_2)_b PO_3 HT$, —$(CH_2)_a NHCONH (CH_2)_b PO_3 T_2$, —$(CH_2)_a NHCSNH(CH_2)_b PO_3 HT$, —$(CH_2)_a NHCSNH(CH_2)_b PO_3 T_2$, —$(CH_2)_a OCON H(CH_2)_b PO_3 HT$, and —$(CH_2)_a OCON H(CH_2)_b PO_3 T_2$, —$(CH_2 —O CH_2)_c —CH_2 —OH$, —$(CH_2)_d —CO_2 T$, —$CH_2 —(CH_2 —O —CH_2)_e —CH_2 —CO_2 T$, —$(CH_2)_f —NH_2$, —$CH_2 —(CH_2 —O —CH_2)_g —CH_2 —NH_2$, —$(CH_2)_h —N(R_b) —(CH_2)_i —CO_2 T$, and —$(CH_2)_j —N(R_b) —CH_2 —(CH_2 —O —CH_2)_k —CH_2 —CO_2 T$; $W_1$ is selected from the group consisting of —$CR_c R_d$, —O—, —$NR_c$, —S—, and —Se; a, b, d, f, h, i, and j independently vary from 1–10; c, e, g, and k independently vary from 1–100; $R_a$, $R_b$, $R_c$, and $R_d$ are defined in the same manner as $Y_1$; T is either H or a negative charge.

The present invention also relates to the novel compounds comprising benzoindoles of general Formula 2

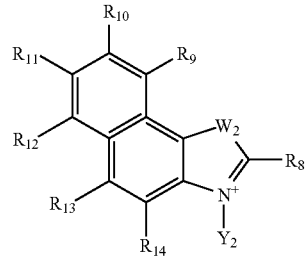

Formula 2 wherein $R_8$, $R_9$, $R_{10}$, $R_{11}$, $R_{12}$, $R_{13}$, $R_{14}$, and $Y_2$ are independently selected from the group consisting of —H, C1–C10 alkoxyl, C1–C10 polyalkoxyalkyl, C1–C20 polyhydroxyalkyl, C5–C20 polyhydroxyaryl, glucose derivatives of R groups, saccharides, amino, C1–C10 aminoalkyl, cyano, nitro, halogen, hydrophilic peptides, arylpolysulfonates, C1–C10 alkyl, C1–C10 aryl, —$SO_3T$, —$CO_2T$, —OH, —$(CH_2)_a SO_3T$, —$(CH_2)_a OSO_3T$, —$(CH_2)_a$ NHSO$_3$T, —(CH$_2$)$_a$CO$_2$(CH$_2$)$_b$SO$_3$T, —(CH$_2$)$_a$OCO(CH$_2$)$_b$ SO$_3$T, —(CH$_2$)$_a$CONH (CH$_2$)$_b$SO$_3$T, —(CH$_2$)$_a$NHCO (CH$_2$)$_b$SO$_3$T, —(CH$_2$)$_a$NHCONH(CH$_2$)$_b$SO$_3$T, —(CH$_2$)$_a$ NHCSNH(CH$_2$)$_b$SO$_3$T, —(CH$_2$)$_a$OCONH(CH$_2$)$_b$SO$_3$T, —(CH$_2$)$_a$PO$_3$HT, —(CH$_2$)$_a$PO$_3$T$_2$, —(CH$_2$)$_a$OPO$_3$HT, —(CH$_2$)$_a$OPO$_3$T$_2$, —(CH$_2$)$_a$NHPO$_3$HT, —(CH$_2$)$_a$NH PO$_3$T$_2$, —(CH$_2$)$_a$CO$_2$(CH$_2$)$_b$PO$_3$HT, —(CH$_2$)$_a$CO$_2$(CH$_2$)$_b$ PO$_2$T$_2$, —(CH$_2$)$_a$OCO(CH$_2$)$_b$PO$_3$HT, —(CH$_2$)$_a$OCO (CH$_2$)$_b$ PO$_3$T$_2$, —(CH$_2$)$_a$CON H(CH$_2$)$_b$PO$_3$HT, —(CH$_2$)$_a$ CON H(CH$_2$)$_b$PO$_3$T$_2$, —(CH$_2$)$_a$NHCO(CH$_2$)$_b$PO$_3$HT, —(CH$_2$)$_a$ NHCO(CH$_2$)$_b$PO$_3$T$_2$, —(CH$_2$)$_a$NHCONH(CH$_2$)$_b$ PO$_3$HT, —(CH$_2$)$_a$NHCONH(CH$_2$)$_b$PO$_3$T$_2$, —(CH$_2$)$_a$NHC-SNH(CH$_2$)$_b$PO$_3$HT, —(CH$_2$)$_a$NHCSNH(CH$_2$)$_b$PO$_3$T$_2$, —(CH$_2$)$_a$ OCONH(CH$_2$)$_b$PO$_3$HT, and —(CH$_2$)$_a$OCONH (CH$_2$)$_b$ PO$_3$T$_2$, —CH$_2$(CH$_2$—O —CH$_2$)$_c$—CH$_2$—OH, —(CH$_2$)$_d$—CO$_2$T, —CH$_2$—(CH$_2$—O—CH$_2$)$_e$—CH$_2$—CO$_2$T, —(CH$_2$)$_f$—NH$_2$, —CH$_2$—(CH$_2$—O—CH$_2$)$_g$—CH$_2$—NH$_2$, —(CH$_2$)$_h$—N(R$_a$)—(CH$_2$)$_i$—CO$_2$T, and —(CH$_2$)$_j$—N(R$_b$) CH$_2$—(CH$_2$—O—CH$_2$)$_k$—CH$_2$—CO$_2$T; W$_2$ is selected from the group consisting of —CR$_c$R$_d$, —O—, —NR$_c$, —S—, and —Se; a, b, d, f, h, i, and j independently vary from 1–10; c, e, g, and k independently vary from 1–100; R$_a$, R$_b$, R$_c$, and R$_d$ are defined in the same manner as Y$_2$; T is either H or a negative charge.

The present invention also relates to the novel compounds comprising cyanine dyes of general Formula 3

Formula 3

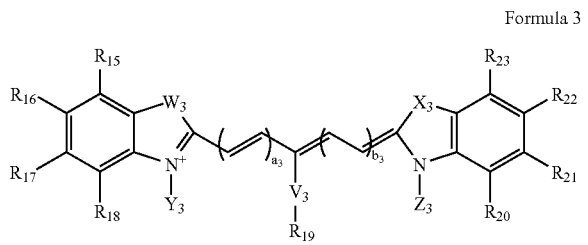

wherein R$_{15}$, R$_{16}$, R$_{17}$, R$_{18}$, R$_{19}$, R$_{20}$, R$_{21}$, R$_{22}$, R$_{23}$, Y$_3$, and Z$_3$ are independently selected from the group consisting of —H, C1–C10 alkoxyl, C1–C10 polyalkoxyalkyl, C1–C20 polyhydroxyalkyl, C5–C20 polyhydroxyaryl, glucose derivatives of R groups, saccharides, amino, C1–C10 aminoalkyl, cyano, nitro, halogen, hydrophilic peptides, arylpolysulfonates, C1–C10 alkyl, C1–C10 aryl, —SO$_3$T, —CO$_2$T, —OH, —(CH$_2$)$_a$SO$_3$T, —(CH$_2$)$_a$OSO$_3$T, —(CH$_2$)$_a$ NHSO$_3$T, —(CH$_2$)$_a$CO$_2$(CH$_2$)$_b$SO$_3$T, —(CH$_2$)$_a$ OCO(CH$_2$(CH$_2$)$_b$SO$_3$T, —(CH$_2$)$_a$CON H(CH$_2$)$_b$SO$_3$T, —(CH$_2$)$_a$NHCO(CH$_2$)$_b$SO$_3$T, —(CH$_2$)$_a$NHCONH(CH$_2$)$_b$ SO$_3$T, —(CH$_2$)$_a$NHCSNH(CH$_2$)$_b$SO$_3$T, —(CH$_2$)$_a$OCON H(CH$_2$)$_b$ SO$_3$T, —(CH$_2$)$_a$PO$_3$HT, —(CH$_2$)$_a$PO$_3$T$_2$, —(CH$_2$)$_a$ OPO$_3$HT, —(CH$_2$)$_a$OPO$_3$T$_2$, —(CH$_2$)$_a$ NHPO$_3$HT, —(CH$_2$)$_a$NHPO$_3$T$_2$, —(CH$_2$)$_a$CO$_2$(CH$_2$)$_b$ PO$_3$HT, —(CH$_2$)$_a$ CO$_2$(CH$_2$)$_b$PO$_3$T$_2$, —(CH$_2$)$_a$OCO(CH$_2$)$_b$ PO$_3$HT, —(CH$_2$)$_a$ OCO(CH$_2$)$_b$PO$_3$T$_2$, —(CH$_2$)$_a$CONH (CH$_2$)$_b$PO$_3$HT, —(CH$_2$)$_a$CONH(CH$_2$)$_b$PO$_3$T$_2$, —(CH$_2$)$_a$ NHCO(CH$_2$)$_b$ PO$_3$HT, —(CH$_2$)$_a$NHCO(CH$_2$)$_b$PO$_3$T$_2$, —(CH$_2$)$_a$NHCONH(CH$_2$)$_b$PO$_3$HT, —(CH$_2$)$_a$NHCONH (CH$_2$)$_b$PO$_3$T$_2$, —(CH$_2$)$_a$NHCSNH(CH$_2$)$_b$PO$_3$HT, —(CH$_2$)$_a$ NHCSNH(CH$_2$)$_b$PO$_3$T$_2$, —(CH$_2$)$_a$OCONH(CH$_2$)$_b$PO$_3$HT, and —(CH$_2$)$_a$OCONH(CH$_2$)$_b$PO$_3$T$_2$, —CH$_2$(CH$_2$—O—CH$_2$)$_c$—CH$_2$—OH, —(CH$_2$)$_d$—CO$_2$T, —CH$_2$—(CH$_2$—O—CH$_2$)$_e$—CH$_2$—CO$_2$T, —(CH$_2$)$_f$—NH$_2$, —CH$_2$—(CH$_2$—O—CH$_2$)$_g$—CH$_2$—CH$_2$—NH$_2$, —(CH$_2$)$_h$—N(R$_a$)—(CH$_2$)$_i$—CO$_2$T, and —(CH$_2$)$_j$—N(R$_b$)—CH$_2$—(CH$_2$—O—CH$_2$)$_k$—CH$_2$—CO$_2$T; W$_3$ and X$_3$ are selected from the group consisting of —CR$_c$R$_d$, —O—, —NR$_c$, —S—, and —Se; V$_3$ is a single bond or is selected from the group consisting of —O—, —S—, —Se—, and —NR$_a$; a, b, d, f, h, i, and j independently vary from 1–10; c, e, g, and k independently vary from 1–100; a$_3$ and b$_3$ vary from 0 to 5; R$_a$, R$_b$, R$_c$, and R$_d$ are defined in the same manner as Y$_3$; T is either H or a negative charge.

The present invention further relates to the novel compounds comprising cyanine dyes of general Formula 4

Formula 4

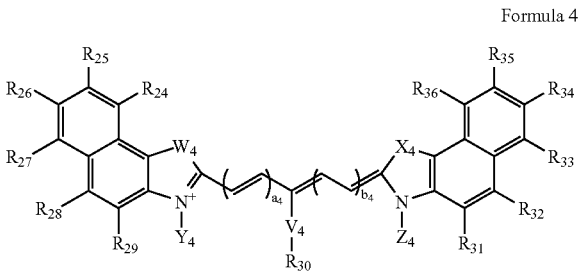

wherein R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, Y$_4$, and Z$_4$ are independently selected from the group consisting of —H, C1–C10 alkoxyl, C1–C10 polyalkoxyalkyl, C1–C20 polyhydroxyalkyl, C5–C20 polyhydroxyaryl, glucose derivatives of R groups, saccharides, amino, C1–C10 aminoalkyl, cyano, nitro, halogen, hydrophilic peptides, arylpolysulfonates, C1–C10 alkyl, C1–C10 aryl, —SO$_3$T, —CO$_2$T, —OH, —(CH$_2$)$_a$SO$_3$T, —(CH$_2$)$_a$ OSO$_3$T, —(CH$_2$)$_a$NHSO$_3$T, —(CH$_2$)$_a$CO$_2$(CH$_2$)$_b$SO$_3$T, —(CH$_2$)$_a$OCO(CH$_2$)$_b$SO$_3$T, —(CH$_2$)$_a$CON H(CH$_2$)$_b$SO$_3$T, —(CH$_2$)$_a$NHCO(CH$_2$)$_b$SO$_3$T, —(CH$_2$)$_a$NHCONH(CH$_2$)$_b$ SO$_3$T, —(CH$_2$)$_a$NHCSNH(CH$_2$)$_b$SO$_3$T, —(CH$_2$)$_a$OCONH (CH$_2$)$_b$SO$_3$T, —(CH$_2$)$_a$PO$_3$HT, —(CH$_2$)$_a$PO$_3$T$_2$, —(CH$_2$)$_a$ OPO$_3$HT, —(CH$_2$)$_a$OPO$_3$T$_2$, —(CH$_2$)$_a$NHPO$_3$HT, —(CH$_2$)$_a$ NHPO$_3$T$_2$, —(CH$_2$)$_a$CO$_2$(CH$_2$)$_b$PO$_3$HT, —(CH$_2$)$_a$ CO$_2$(CH$_2$)$_b$PO$_3$T$_2$, —(CH$_2$)$_a$OCO(CH$_2$)$_b$PO$_3$HT, —(CH$_2$)$_a$ OCO(CH$_2$)$_b$PO$_3$T$_2$, —(CH$_2$)$_a$CONH(CH$_2$)$_b$ PO$_3$HT, —(CH$_2$)$_a$CONH(CH$_2$)$_b$PO$_3$T$_2$, —(CH$_2$)$_a$NHCO (CH$_2$)$_b$ PO$_3$HT, —(CH$_2$)$_a$NHCO(CH$_2$)$_b$PO$_3$T$_2$, —(CH$_2$)$_a$N-HCONH(CH$_2$)$_b$PO$_3$HT, —(CH$_2$)$_a$NHCONH(CH$_2$)$_b$PO$_3$T$_2$, —(CH$_2$)$_a$NHCSNH(CH$_2$)$_b$PO$_3$HT, —(CH$_2$)$_a$NHCSNH (CH$_2$)$_b$PO$_3$T$_2$, —(CH$_2$)$_a$OCONH(CH$_2$)$_b$PO$_3$HT, and —(CH$_2$)$_a$OCONH(CH$_2$)$_b$PO$_3$T$_2$, —CH$_2$(CH$_2$—O—CH$_2$)$_c$—CH$_2$—OH, —(CH$_2$)$_d$—CO$_2$T, —CH$_2$—(CH$_2$—O—CH$_2$)$_e$—CH$_2$—CO$_2$T, —(CH$_2$)$_f$—NH$_2$, —CH$_2$—(CH$_2$—O—CH$_2$)$_g$—CH$_2$—NH$_2$, —(CH$_2$)$_h$—N(R$_a$)—(CH$_2$)$_i$—CO$_2$T, and —(CH$_2$)$_j$—N(R$_b$)—CH$_2$—(CH$_2$—O—CH$_2$)$_k$—CH$_2$—CO$_2$T; W$_4$ and X4 are selected from the group consisting of —CR$_c$R$_d$, —O—, —NR$_c$, —S—, and —Se; V$_4$ is a single bond or is selected from the group consisting of —O—, —S—, —Se—, and —NR$_a$; a$_4$ and b$_4$ vary from 0 to 5; a, b, d, f, h, i, and j independently vary from 1–10; c, e, g, and k independently vary from 1–100; R$_a$, R$_b$, R$_c$, and R$_d$ are defined in the same manner as Y$_4$; T is either H or a negative charge.

The present invention also relates to the novel compounds comprising cyanine dyes of general Formula 5

Formula 5

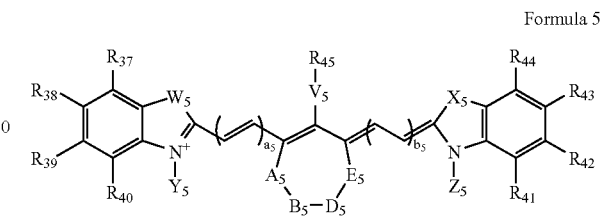

wherein R$_{37}$, R$_{38}$, R$_{39}$, R$_{40}$, R$_{41}$, R$_{42}$, R$_{43}$, R$_{44}$, R$_{45}$, Y$_5$, and Z$_5$ are independently selected from the group consisting of —H, C1–C10 alkoxyl, C1–C10 polyalkoxyalkyl, C1–C20 polyhydroxyalkyl, C5–C20 polyhydroxyaryl, glucose derivatives of R groups, saccharides, amino, C1–C10 aminoalkyl, cyano, nitro, halogen, hydrophilic peptides, arylpolysulfonates, C1–C10 alkyl, C1–C10 aryl, —$SO_3T$, —$CO_2T$, —OH, —$(CH_2)_aSO_3T$, —$(CH_2)_aOSO_3T$, —$(CH_2)_a NHSO_3T$, —$(CH_2)_aCO_2(CH_2)_bSO_3T$, —$(CH_2)_a OCO(CH_2)_b SO_3T$, —$(CH_2)_aCONH(CH_2)_bSO_3T$, —$(CH_2)_a NHCO(CH_2)_bSO_3T$, —$(CH_2)_aNHCONH(CH_2)_bSO_3T$, —$(CH_2)_a NHCSNH(CH_2)_bSO_3T$, —$(CH_2)_aOCONH(CH_2)_b SO_3T$, —$(CH_2)_aPO_3HT$, —$(CH_2)_aPO_3T_2$, —$(CH_2)_a OPO_3HT$, —$(CH_2)_aOPO_3T_2$, —$(CH_2)_aNHPO_3HT$, —$(CH_2)_a NHPO_3T_2$, —$(CH_2)_aCO_2(CH_2)_bPO_3HT$, —$(CH_2)_a CO_2(CH_2)_bPO_3T_2$, —$(CH_2)_aOCO(CH_2)_bPO_3HT$, —$(CH_2)_a OCO(CH_2)_bPO_3T_2$, —$(CH_2)_aCONH(CH_2)_b PO_3HT$, —$(CH_2)_aCONH(CH_2)_bPO_3T_2$, —$(CH_2)_aNHCO(CH_2)_b PO_3HT$, —$(CH_2)_aNHCO(CH_2)_bPO_3T_2$, —$(CH_2)_aN\text{-}HCONH(CH_2)_bPO_3HT$, —$(CH_2)_aNHCONH(CH_2)_bPO_3T_2$, —$(CH_2)_aNHCSNH(CH_2)_bPO_3HT$, —$(CH_2)_aNHCSNH(CH_2)_bPO_3T_2$, —$(CH_2)_aOCONH(CH_2)_bPO_3HT$, and —$(CH_2)_aOCONH(CH_2)_bPO_3T_2$, —$CH_2(CH_2$—O—$CH_2)_c$—$CH_2$—OH, —$(CH_2)_d$—$CO_2T$, —$CH_2$—$(CH_2$—O—$CH_2)_e$—$CH_2$—$CO_2T$, —$(CH_2)_f$—$NH_2$, —$CH_2$—$(CH_2$—O—$)_g$—$CH_2$—$NH_2$, —$(CH_2)_h$—$N(R_a)$—$(CH_2)_i$—$CO_2T$, and —$(CH_2)_j$—$N(R_b)$—$CH_2$—$(CH_2$—O—$CH_2)_k$—$CH_2$—$CO_2T$; $W_5$ and $X_5$ are selected from the group consisting of —$CR_cR_d$, —O—, —$NR_c$, —S—, and —Se; $V_5$ is a single bond or is selected from the group consisting of —O—, —S—, —Se—, and —$NR_a$; D5 is a single or a double bond; $A_5$, $B_5$ and $E_5$ may be the same or different and are selected from the group consisting of —O—, —S—, —Se—, —P—, —$NR_a$, —$CR_cR_d$, $CR_c$, alkyl, and —C=O; $A_5$, $B_5$, $D_5$, and $E_5$ may together form a 6 or 7 membered carbocyclic ring or a 6 or 7 membered heterocyclic ring optionally containing one or more oxygen, nitrogen, or a sulfur atom; a, b, d, f, h, i, and j independently vary from 1–10; c, e, g, and k independently vary from 1–100; $a_5$ and $b_5$ vary from 0 to 5; $R_a$, $R_b$, $R_c$, and $R_d$ are defined in the same manner as $Y_5$; T is either H or a negative charge.

The present invention also relates to the novel compounds comprising cyanine dyes of general Formula 6

—$(CH_2)_aOCO(CH_2)_bSO_3T$, —$(CH_2)_aCONH(CH_2)_bSO_3T$, —$(CH_2)_aNHCO(CH_2)_bSO_3T$, —$(CH_2)_aNHCONH(CH_2)_b SO_3T$, —$(CH_2)_aNHCSNH(CH_2)_bSO_3T$, —$(CH_2)_aOCONH (CH_2)_bSO_3T$, —$(CH_2)_aPO_3HT$, —$(CH_2)_aPO_3T_2$, —$(Ch_2)_a OPO_3HT$, —$(CH_2)_aOPO_3T_2$, —$(CH_2)_aNHPO_3HT$, —$(CH_2)_a NHPO_3T_2$, —$(CH_2)_aCO_2(CH_2)_bPO_3HT$, —$(CH_2)_a CO_2(CH_2)_bPO_3T_2$, —$(CH_2)_aOCO(CH_2)_bPO_3HT$, —$(CH_2)_a OCO(CH_2)_bPO_3T_2$, —$(CH_2)_aCONH(CH_2)_b PO_3HT$, —$(CH_2)_aCONH(CH_2)_bPO_3T_2$, —$(CH_2)_aNHCO (CH_2)_b PO_3HT$, —$(CH_2)_aNHCO(CH_2)_bPO_3T_2$, —$(CH_2)_aN\text{-}HCONH(CH_2)_bPO_3HT$, —$(CH_2)_aNHCONH(CH_2)_bPO_3T_2$, —$(CH_2)_aNHCSNH(CH_2)_bPO_3HT$, —$(CH_2)_aNHCSNH (CH_2)_bPO_3T_2$, —$(CH_2)_aOCONH(CH_2)_bPO_3HT$, and —$(CH_2)_aOCONH(CH_2)_bPO_3T_2$, —$CH_2(CH_2$—O—$CH_2)_c$—$CH_2$—OH, —$(CH_2)_d$—$CO_2T$, —$CH_2$—$(CH_2$—O—$CH_2)_e$—$CH_2$—$CO_2T$, —$(CH_2)_f$$NH_2$, —$CH_2$—$(CH_2$—O—$CH_2)_g$—$CH_2$—$NH_2$, —$(CH_2)_h$—$N(R_a)$—$(CH_2)_i$—$CO_2T$, and —$(CH_2)_j$—$N(R_b)$—$CH_2$—$(Ch_2$—O—$CH_2)_k$—$Ch_2$—$CO_2T$; $W_6$ and $X_6$ are selected from the group consisting of —$CR_cR_d$, —O—, —$NR_c$, —S—, and —Se; $V_6$ is a single bond or is selected from the group consisting of —O—, —S—, —Se—, and —$NR_a$; D6 is a single or a double bond; A6, $B_6$ and $E_6$ may be the same or different and are selected from the group consisting of —O—, —S—, —Se—, —P—, —$NR_a$, —$CR_cR_d$, $CR_c$, alkyl, and —C=O; $A_6$, $B_6$, $D_6$, and $E_6$ may together form a 6 or 7 membered carbocyclic ring or a 6 or 7 membered heterocyclic ring optionally containing one or more oxygen, nitrogen, or sulfur atom; a, b, d, f, h, i, and j independently vary from 1–10; c, e, g, and k independently vary from 1–100; $a_6$ and $b_6$ vary from 0 to 5; $R_a$, $R_b$, $R_c$, and $R_d$ are defined in the same manner as $Y_6$; T is either H or a negative charge.

A hydrophilic chelate such as ethylenediaminetetraacetic acid (EDTA), diethylenetriaminepentaacetic acid (DPTA), 1,4,7,10-tetraazacyclododecanetetraacetic acid (DOTA), or their derivatives, can be attached to the compounds of Formula 6

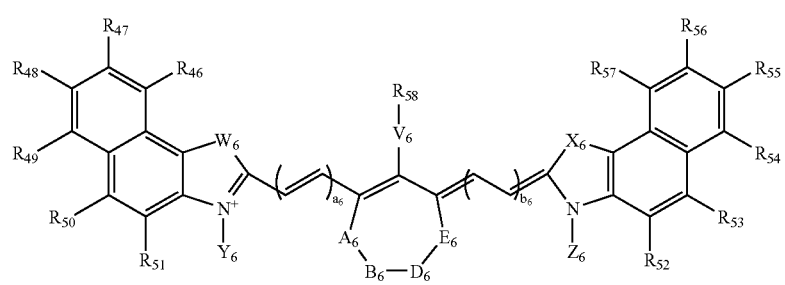

wherein $R_{46}$, $R_{47}$, $R_{49}$, $R_{49}$, $R_{50}$, $R_{51}$, $R_{52}$, $R_{53}$, $R_{54}$, $R_{55}$, $R_{56}$, $R_{57}$ and $R_{58}$, $Y_6$, and $Z_6$ are independently selected from the group consisting of —H, C1–C10 alkoxyl, C1–C10 polyalkoxyalkyl, C1–C20 polyhydroxyalkyl, $C_5$–$C_{20}$ polyhydroxyaryl, glucose derivatives of R groups, saccharides, amino, C1–C10 aminoalkyl, cyano, nitro, halogen, hydrophilic peptides, arylpolysulfonates, C1–C10 alkyl, C1–C10 aryl, —$SO_3T$, —$CO_2T$, —OH, —$(CH_2)_aSO_3T$, —$(CH_2)_a OSO_3T$, —$(CH_2)_aNHSO_3T$, —$(CH_2)_aCO_2(CH_2)_bSO_3T$, Formulas 1–6 as one or more R groups. These structures are expected to be highly water soluble.

The inventive compounds, compositions, and methods are advantageous since they provide a real-time, accurate, repeatable measure of renal excretion rate using exogenous markers under specific yet changing circumstances. This represents a substantial improvement over any currently available or widely practiced method, since currently, no reliable, continuous, repeatable bedside method for the assessment of specific renal function by optical methods exists. Moreover, since the inventive method depends solely on the renal elimination of the exogenous chemical entity, the measurement is absolute and requires no subjective interpretation based on age, muscle mass, blood pressure, etc. In fact it represents the nature of renal function in a particular patient, under these particular circumstances, at a precise moment in time.

The inventive compounds, compositions, and methods provide simple, efficient, and effective monitoring of organ function. The compound is administered and a sensor, either external or internal, is used to detect absorption and/or emission to determine the rate at which the compound is cleared from the blood. By altering the R groups, the compounds may be rendered more organ specific.

BRIEF DESCRIPTION OF THE DRAWINGS

FIG. 1: Reaction pathway for the preparation of indole derivatives.

FIG. 2: Reaction pathway for the preparation of benzoindole derivatives.

DETAILED DESCRIPTION

Figure 3:
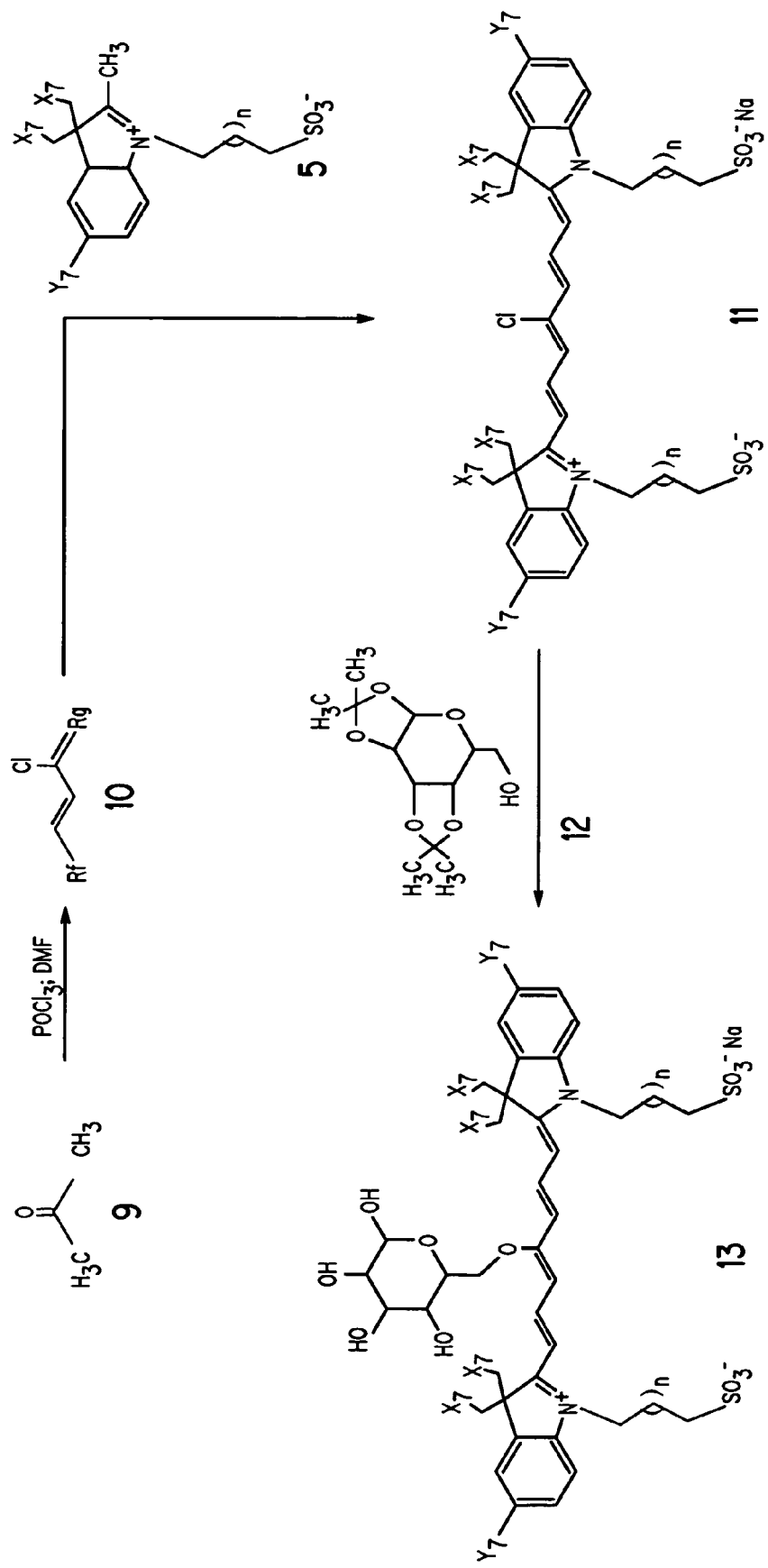
FIG. 3: Reaction pathway for the preparation of indocarbocyanine derivatives.

In one embodiment the dyes of the invention serve as probes for continuous monitoring of renal function, especially for critically ill patients and kidney transplant patients.

In another embodiment, the dyes of the invention are useful for dynamic hepatic function monitoring, especially for critically ill patients and liver transplant patients.

In another embodiment, the dyes of the invention are useful for real-time determination of cardiac function, especially in patients with cardiac diseases.

In another embodiment, the dyes of the invention are useful for monitoring organ perfusion, especially for critically ill, cancer, and organ transplant patients.

In another embodiment, the dyes are useful for assessing the functional status of tumors and for monitoring tumor perfusion, such as in renal or hepatic cancer patients.

The novel dyes of the present invention are prepared according to the methods well known in the art, as illustrated in general in FIGS. 1–7 and described for specific compounds in Examples 1–11.

In one embodiment, the novel compounds, also called tracers, of the present invention have the Formula 1, wherein $R_3$, $R_4$, $R_5$, $R_6$ and $R_7$, and $Y_1$ are independently selected from the group consisting of —H, C1–C5 alkoxyl, C1–C5 polyalkoxyalkyl, C1–C10 polyhydroxyalkyl, C5–C20 polyhydroxyaryl, mono- and disaccharides, nitro, hydrophilic peptides, arylpolysulfonates, C1–C5 alkyl, C1–C10 aryl, —SO$_3$T, —CO$_2$T, —OH, —(CH$_2$)$_a$SO$_3$T, —(CH$_2$)$_a$OSO$_3$T, —(CH$_2$)$_a$NHSO$_3$T, —(CH$_2$)$_a$CO$_2$(CH$_2$)$_b$SO$_3$T, —(CH$_2$)$_a$OCO(CH$_2$)$_b$SO$_3$T, —CH$_2$(CH$_2$—O—CH$_2$)$_c$—CH$_2$—OH, —(CH$_2$)$_d$—CO$_2$T, —CH$_2$—(CH$_2$—O—CH$_2$)$_e$—CH$_2$—CO$_2$T, —(CH$_2$)$_f$—NH$_2$, —CH$_2$—(CH$_2$—O—Ch$_2$)$_g$—CH$_2$—NH$_2$, —(CH$_2$)$_h$, —N(R$_a$)—(CH$_2$)$_i$—CO$_2$T, and —(CH$_2$)$_j$—N(R$_b$)—CH$_2$—(CH$_2$—O—CH$_2$)$_k$—Ch$_2$—CO$_2$T; $W_1$ is selected from the group consisting of —CR$_c$R$_d$, —O—, —NR$_c$, —S—, and —Se; a, b, d, f, h, l, and j independently vary from 1–5; c, e, g, and k independently vary from 1–20; $R_a$, $R_b$, $R_c$, and $R_d$ are defined in the same manner as $Y_1$; T is a negative charge.

In another embodiment, the novel compounds of the present invention have the general Formula 2, wherein $R_8$, $R_9$, $R_{10}$, $R_{11}$, $R_{12}$, $R_{13}$, $R_{14}$, and $Y_2$ are independently selected from the group consisting of —H, C1–C5 alkoxyl, C1–C5 polyalkoxyalkyl, C1–C10 polyhydroxyalkyl, C5–C20 polyhydroxyaryl, mono- and disaccharides, nitro, hydrophilic peptides, arylpolysulfonates, C1–C5 alkyl, C1–C10 aryl, —SO$_3$T, —CO$_2$T, —OH, —(CH$_2$)$_a$SO$_3$T, —(CH$_2$)$_a$OSO$_3$T, —(CH$_2$)$_a$NHSO$_3$T, —(CH$_2$)$_a$CO$_2$(CH$_2$)$_b$—SO$_3$T, —(CH$_2$)$_a$OCO(CH$_2$)$_b$SO$_3$T, —CH$_2$(CH$_2$—C—CH$_2$)C—CH$_2$—OH, —(CH$_2$)$_d$—CO$_2$T, —CH$_2$—(CH$_2$—O—CH$_2$)$_e$—CH$_2$—CO$_2$T, —(CH$_2$)$_f$N H$_2$, —CH$_2$—(CH$_2$—O—CH$_2$)$_g$—CH$_2$—NH$_2$, —(CH$_2$)$_h$—N(R$_a$)—(CH$_2$)$_i$—CO$_2$T, and —(CH$_2$)$_j$—N(R$_b$)—CH$_2$—(CH$_2$—O—CH$_2$)$_k$—CH$_2$—CO$_2$T; $W_2$ is selected from the group consisting of —CR$_c$R$_d$, —O—, —NR$_c$, —S—, and —Se; a, b, d, f, h, l, and j independently vary from 1–5; c, e, g, and k independently vary from 1–20; $R_a$, $R_b$, $R_c$, and $R_d$ are defined in the same manner as $Y_2$; T is a negative charge.

In another embodiment, the novel compositions of the present invention have the general Formula 3, wherein $R_{15}$, $R_{16}$, $R_{17}$, $R_{18}$, $R_{19}$, $R_{20}$, $R_{21}$, $R_{22}$, $R_{23}$, $Y_3$, and $Z_3$ are independently selected from the group consisting of —H, C1–C5 alkoxyl, C1–C5 polyalkoxyalkyl, C1-C10 polyhydroxyalkyl, C5–C20 polyhydroxyaryl, mono- and disaccharides, nitro, hydrophilic peptides, arylpolysulfonates, C1–C5 alkyl, C1–C10 aryl, —SO$_3$T, —CO$_2$T, —OH, —(CH$_2$)$_a$SO$_3$T, —(CH$_2$)$_a$OSO$_3$T, —(CH$_2$)$_a$NHSO$_3$T, —(CH$_2$)$_a$CO$_2$(CH$_2$)$_b$SO$_3$T, —(CH$_2$)$_a$OCO(CH$_2$)$_b$SO$_3$T, —CH$_2$(CH$_2$—O—CH$_2$)$_c$—CH$_2$—OH, —(CH$_2$)$_d$—CO$_2$T, —CH$_2$—(CH$_2$—O—CH$_2$)$_e$—CH$_2$—CO$_2$T, —(CH$_2$)$_f$—NH$_2$, —CH$_2$—(CH$_2$—O—CH$_2$)$_g$—CH$_2$NH$_2$, —(CH$_2$)$_h$—N(R$_a$)—(CH$_2$)$_i$—CO$_2$T, and —(CH$_2$)$_j$—N(R$_b$)—CH$_2$—(CH$_2$—O—CH$_2$)$_k$—CH$_2$—CO$_2$T; $W_3$ and $X_3$ are selected from the group consisting of —CR$_c$R$_d$, —O—, —NR$_c$, —S—, and —Se; $V_3$ is a single bond or is selected from the group consisting of —O—, —S—, —Se—, and —NR$_a$; a, b, d, f, h, i, and j independently vary from 1–5; c, e, g, and k independently vary from 1–50; $a_3$ and $b_3$ vary from 0 to 5;

$R_a$, $R_b$, $R_c$, and $R_d$ are defined in the same manner as $Y_3$; T is either H or a negative charge.

In another embodiment, the novel compounds of the present invention have the general Formula 4, wherein $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $Y_4$, and $Z_4$ are independently selected from the group consisting of —H, C1–C5 alkoxyl, C1–C5 polyalkoxyalkyl, C1–C10 polyhydroxyalkyl, C5–C20 polyhydroxyaryl, mono- and disaccharides, nitro, hydrophilic peptides, arylpolysulfonates, C1–C5 alkyl, C1–C10 aryl, —$SO_3T$, —$CO_2T$, —OH, —$(CH_2)_aSO_3T$, —$(CH_2)_aOSO_3T$, —$(CH_2)_a$ $NHSO_3T$, —$(CH_2)_aCO_2(CH_2)_bSO_3T$, —$(CH_2)_a$ $OCO(CH_2)_b$ $SO_3T$, —$CH_2(CH_2$—O—$CH_2)_c$—$CH_2$—OH, —$(CH_2)_d$—$CO_2T$, —$CH_2$—$(CH_2$—O—$CH_2)_e$—$CH_2$—$CO_2T$, —$(CH_2)_f$—$NH_2$, —$CH_2$—$(CH_2$—O—$CH_2)_g$—$CH_2$—$NH_2$, —$(CH_2)_h$—$N(R_a)$—$(CH_2)_i$—$CO_2T$, and —$(CH_2)_j$—$N(R_b)$—$CH_2$—O—$CH_2)_k$—$CH_2$—$CO_2T$; $W_4$ and $X_4$ are selected from the group consisting of —$CR_cR_d$, —O—, —$NR_c$, —S—, and —Se; $V_4$ is a single bond or is selected from the group consisting of —O—, —S—, —Se—, and —$NR_a$; $a_4$ and $b_4$ vary from 0 to 5; a, b, d, f, h, i, and j independently vary from 1–5; c, e, g, and k independently vary from 1–50; $R_a$, $R_b$, $R_c$, and $R_d$ are defined in the same manner as $Y_4$; T is either H or a negative charge.

In another embodiment, the novel compounds of the present invention have the general Formula 5, wherein $R_{37}$, $R_{38}$, $R_{39}$, $R_{40}$, $R_{41}$, $R_{42}$, $R_{43}$, $R_{44}$, $R_{45}$, $Y_5$, and $Z_5$ are independently selected from the group consisting of —H, C1–C5 alkoxyl, C1–C5 polyalkoxyalkyl, C1–C10 polyhydroxyalkyl, C5–C20 polyhydroxyaryl, mono- and disaccharides, nitro, hydrophilic peptides, arylpolysulfonates, C1–C5 alkyl, C1–C10 aryl, —$SO_3T$, —$CO_2T$, —OH, —$(CH_2)_a$ $SO_3T$, —$(CH_2)_aOSO_3T$, —$(CH_2)_aNHSO_3T$, —$(CH_2)_aCO_2$ $(CH_2)_bSO_3T$, —$(CH_2)_aOCO(CH_2)_bSO_3T$, —$CH_2(CH_2$—O—$CH_2)_c$—$CH_2$—OH, —$(CH_2)_d$—$CO_2T$, —$CH_2$—$(CH_2$—O—$CH_2)_e$—$CH_2$—$CO_2T$, —$(CH_2)_f$—$NH_2$, —$CH_2$—$(CH_2$—O—$CH_2)_g$—$CH_2$—$NH_2$, —$(CH_2)_h$—$N(R_a)$—$(CH_2)_i$—$CO_2T$, and —$(CH_2)_j$—$N(R_b)$—$CH_2$—$(CH_2$—O—$CH_2)_k$—$CH_2$—$CO_2T$; $W_5$ and $X_5$ are selected from the group consisting of —$CR_cR_d$, —O—, —$NR_c$, —S—, and —Se; $V_5$ is a single bond or is selected from the group consisting of —O—, —S—, —Se—, and —$NR_a$ $D_5$ is a single or a double bond; $A_5$, $B_5$ and $E_5$ may be the same or different and are selected from the group consisting of —O—, —S—, —$NR_a$, —$CR_cR_d$, $CR_c$, and alkyl; $A_5$, $B_5$, $D_5$, and $E_5$ may together form a 6 or 7 membered carbocyclic ring or a 6 or 7 membered heterocyclic ring optionally containing one or more oxygen, nitrogen, or sulfur atom; a, b, d, f, h, i, and j independently vary from 1–5; c, e, g, and k independently vary from 1–50; $a_5$ and $b_5$ vary from 0 to 5; $R_a$, $R_b$, $R_c$, and $R_d$ are defined in the same manner as $Y_5$; T is either H or a negative charge.

In yet another embodiment, the novel compounds of the present invention have the general Formula 6, wherein $R_{46}$, $R_{47}$, $R_{48}$, $R_{49}$, $R_{50}$, $R_{51}$, $R_{52}$, $R_{53}$, $R_{54}$, $R_{55}$, $R_{56}$, $R_{57}$, $R_{58}$, $Y_6$, and $Z_6$ are independently selected from the group consisting of —H, C1–C5 alkoxyl, C1–C5 polyalkoxyalkyl, C1–C10 polyhydroxyalkyl, C5–C20 polyhydroxyaryl, mono- and disaccharides, nitro, hydrophilic peptides, arylpolysulfonates, C1–C5 alkyl, C1–C10 aryl, —$SO_3T$, —$CO_2T$, —OH, —$(CH_2)_aSO_3T$, —$(CH_2)_aOSO_3T$, —$(CH_2)_a$ $NHSO_3T$, —$(CH_2)_aCO_2(CH_2)_bSO_3T$, —$(CH_2)_a$ $OCO(CH_2)_bS$ \$O_3T$, —$CH_2(CH_2$—O—$CH_2)_c$—$CH_2OH$, —$(CH_2)_d$—$CO_2T$, —$CH_2$—$(CH_2$—O—$CH_2)_e$—$CH_2$—$CO_2T$, —$(CH_2)_f$—$NH_2$, —$CH_2$—$(CH_2$—O —$CH_2)_g$—$CH_2$—$NH_2$, —$(CH_2)_h$—$N(R_a)$—$(CH_2)_i$—$CO_2T$, and —$(CH_2)_j$—$N(R_b)$—$CH_2$—$(CH_2$—O —$CH_2)_k$—$CH_2$—$CO_2T$; $W_6$ and $X_6$ are selected from the group consisting of —$CR_cR_d$, —O—, —$NR_c$, —S—, and —Se; $V_6$ is a single bond or is selected from the group consisting of —O—, —S—, —Se—, and —$NR_a$; $D_6$ is a single or a double bond; $A_6$, $B_6$ and $E_6$ may be the same or different and are selected from the group consisting of —O—, —S—, —$NR_a$, —$CR_c$ $R_d$, $CR_c$, and alkyl; A, $B_6$, $D_6$, and $E_6$ may together form a 6 or 7 membered carbocyclic ring or a 6 or 7 membered heterocyclic ring optionally containing one or more oxygen, nitrogen, or sulfur atom; a, b, d, f, h, i, and j independently vary from 1–5; c, e, g, and k independently vary from 1–50; $a_5$ and $b_5$ vary from 0 to 5; $R_a$, $R_b$, $R_c$, and $R_d$ are defined in the same manner as $Y_6$; T is either H or a negative charge.

The compounds of the invention can be formulated into diagnostic and therapeutic compositions for enteral or parenteral administration. These compositions contain an effective amount of the dye along with conventional pharmaceutical carriers and excipients appropriate for the type of administration contemplated. For example, parenteral formulations advantageously contain the inventive agent in a sterile aqueous solution or suspension. Parenteral compositions may be injected directly or mixed with a large volume parenteral composition for systemic administration. Such solutions also may contain pharmaceutically acceptable buffers and, optionally, electrolytes such as sodium chloride.

Formulations for enteral administration may vary widely, as is well known in the art. In general, such formulations are liquids, which include an effective amount of the inventive agent in aqueous solution or suspension. Such enteral compositions may optionally include buffers, surfactants, thixotropic agents, and the like. Compositions for oral administration may also contain flavoring agents and other ingredients for enhancing their organoleptic qualities.

The compositions are administered in doses effective to achieve the desired effect or result. The dosage of the tracers may vary according to the clinical procedure contemplated and generally ranges from 1 picomolar to 100 millimolar. The compositions may be administered to a patient, typically a warm-blooded animal either systemically or locally to the organ or tissue to be imaged, and the patient then subject to the imaging procedure. The tracers may be administered to the patient by any suitable method, including intravenous, intraperitoneal, or subcutaneous injection or infusion, oral administration, transdermal absorption through the skin, aerosols, or by inhalation. The detection of the tracers is achieved by optical fluorescence, absorbance, or light scattering methods known in the art (Muller et al. Eds., *Medical Optical Tomography*, SPIE Volume IS11, 1993, which is expressly incorporated herein by reference) using invasive or non-invasive probes such as endoscopes, catheters, ear clips, hand bands, surface coils, finger probes, and the like. Physiological function is correlated with the clearance profiles and rates of these agents from body fluids (R. B. Dorshow et al., *Non-Invasive Fluorescence Detection of Hepatic and Renal Function, Bull. Am. Phys. Soc.* 1997, 42, 681, which is expressly incorporated by reference herein).

The inventive composition may be administered for imaging by more than one modality. As one example, the composition may be used for imaging by optical imaging alone, by nuclear imaging alone, or by both optical and nuclear imaging modalities when a radioactive isotope is included in the chemical formula, such as replacing a halogen atom with a radioactive halogen, and/or including a radioactive metal ion such as $Tc^{99}$, $In^{111}$, etc. As another example, the composition may be used for imaging by optical imaging alone, by magnetic resonance (MR) alone, or by both optical and MR modalities when a paramagnetic metal ion such as gadolinium or manganese is included in the chemical formula.

It will also be appreciated that the inventive compositions may be administered with other contrast agents or media used to enhance an image from a non-optical modality. These include agents for enhancing an image obtained by modalities including but not limited to MR, ultrasound (US), x-ray, positron emission tomography (PET), computed tomography (CT), single photon emission computed tomography (SPECT), optoacoustic (e.g. U.S. Pat. Nos. 5,840,023 and 5,977,538 which are expressly incorporated by reference herein in their entirety), etc. Both optical and non-optical agents may be formulated as a single composition (that is, one composition containing one, two, or more components, for example, an optical agent and a MR agent), or may be formulated as separate compositions. The inventive optical imaging contrast agent and the non-optical contrast agent are administered in doses effective to achieve the desired enhancement, diagnosis, therapy, etc., as known to one skilled in the art. The inventive compositions, either alone or combined with a contrast agent, may be administered to a patient, typically a warm-blooded animal, systemically or locally to the organ or tissue to be imaged. The patient is then imaged by optical imaging and/or by another modality. As one example of this embodiment, the inventive compounds may be added to contrast media compositions. As another example, the inventive compositions may be co-administered with contrast media, either simultaneously or within the same diagnostic and/or therapeutic procedure (for example, administering the inventive composition and administering a contrast agent then performing optical imaging followed by another imaging modality, or administering the inventive composition and administering a contrast agent then performing another imaging modality followed by optical imaging, or administering the inventive composition and optical imaging, then administering a contrast agent and MR, US, CT, etc. imaging, or administering a contrast agent and imaging by MR, US, CT, etc., then administering the inventive composition and optical imaging, or administering the inventive composition and a contrast agent, and simultaneously imaging by an optical modality and MR, US, CT, etc.). As another example, an optical imaging agent may be added as an additive or excipient for a non-optical imaging modality. In this embodiment, the optically active component, such as the dyes disclosed herein, could be added as a buffering agent to control pH or as a chelate to improve formulation stability, etc. in MR contrast media, CT contrast media, x-ray contrast media, US contrast media, etc. The MR, CT, x-ray, US contrast media would then also function as an optical imaging agent. The information obtained from the modality using the non-optical contrast agent is useful in combination with the image obtained using the optical contrast agent.

In one embodiment, the agents may be formulated as micelles, liposomes, microcapsules, or other microparticles. These formulations may enhance delivery, and localization of the inventive compounds to/at the desired organ or site. The target specificity of these formulations can be enhanced by using suitable targeting molecules such as peptides, saccharides, fatty acids, etc. Preparation and loading of these are well known in the art.

As one example, liposomes may be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, *Liposome Dermatics*, Springer-Verlag, Berlin (1992)). Polycaprolactone, poly(glycolic) acid, poly(lactic) acid, polyanhydride or lipids may be formulated as microspheres. As an illustrative example, the optical agent may be mixed with polyvinyl alcohol (PVA), the mixture then dried and coated with ethylene vinyl acetate, then cooled again with PVA. In a liposome, the optical agent may be within one or both lipid bilayers, in the aqueous between the bilayers, or with the center or core. Liposomes may be modified with other molecules and lipids to form a cationic liposome. Liposomes may also be modified with lipids to render their surface more hydrophilic which increases their circulation time in the bloodstream. The thus-modified liposome has been termed a "stealth" liposome, or a long-lived liposome, as described in U.S. Pat. Nos. 6,277403; 6,610,322; 5,631,018; 5,395,619; and 6,258,378, each of which is expressly incorporated by reference herein in its entirety, and in *Stealth Liposomes*, Lasic and Martin (Eds.) 1995, CRC Press, London. Encapsulation methods include detergent dialysis, freeze drying, film forming, injection, as known to one skilled in the art and disclosed in, for example, U.S. Pat. No. 6,406,713 which is expressly incorporated by reference herein in its entirety.

The agent formulated in liposomes, microcapsules, etc. may be administered by any of the routes previously described. In a formulation applied topically, the optical agent is slowly released over time. In an injectable formulation, the liposome capsule circulates in the bloodstream and is delivered to a desired site.

As another example, microparticles such as ultra small iron oxide particles (USPIO) and other metallic particles such as silver or gold particles coated with or attached (covalently or non-covalently) with the inventive compounds may be used for optical imaging and/or MRI. Such particles are known to one skilled in the art as disclosed in, for example, U.S. Pat. No. 5,492,814 and Journal of Biomedical Optics 8(3), 472–478 (July 2003) which are expressly incorporated by reference herein in their entirety.

Organ function can be assessed either by the differences in the manner in which the normal and impaired cells remove the tracer from the bloodstream, by measuring the rate or accumulation of these tracers in the organs or tissues, or by obtaining tomographic images of the organs or tissues. Blood pool clearance may be measured non-invasively from convenient surface capillaries such as those found in an ear lobe or a finger, for example, using an ear clip or finger clip sensor, or may be measured invasively using an endovascular catheter. Accumulation of the tracer within the cells of interest can be assessed in a similar fashion. The clearance of the tracer dyes may be determined by selecting excitation wavelengths and filters for the emitted photons. The concentration-time curves may be analyzed in real time by a microprocessor. In order to demonstrate feasibility of the inventive compounds to monitor organ function, a non-invasive absorbance or fluorescence detection system to monitor the signal emanating from the vasculature infused with the compounds is used. Indole derivatives, such as those of Formulas 1–6, fluoresce at a wavelength between 350 nm and 1300 nm when excited at the appropriate wavelength as is known to, or readily determined by, one skilled in the art.

In addition to the noninvasive techniques, a modified pulmonary artery catheter can be used to make the necessary measurements (R. B. Dorshow, J. E. Bugaj, S. A. Achilefu, R. Rajagopalan, and A. H. Combs, *Monitoring Physiological Function by Detection of Exogenous Fluorescent Contrast Agents*, in *Optical Diagnostics of Biological Fluids IV*, A. Priezzhev and T. Asakura, Editors, Proceedings of SPIE 1999, 3599, 2–8, which is expressly incorporated by reference herein). Currently, pulmonary artery catheters measure only intravascular pressures, cardiac output and other derived measures of blood flow. Critically ill patients are managed using these parameters, but rely on intermittent blood sampling and testing for assessment of renal function. These laboratory parameters represent discontinuous data and are frequently misleading in many patient populations. Yet, importantly, they are relied upon heavily for patient assessment, treatment decisions, and drug dosing.

The modified pulmonary artery catheter incorporates an optical sensor into the tip of a standard pulmonary artery catheter. This wavelength specific optical sensor can monitor the renal function specific elimination of an optically detectable chemical entity. Thus, by a method analogous to a dye dilution curve, real-time renal function can be monitored by the disappearance of the optically detected compound. Modification of a standard pulmonary artery catheter only requires making the fiber optic sensor wavelength specific, as is known to one skilled in this art. Catheters that incorporate fiber optic technology for measuring mixed venous oxygen saturation currently exist.

The present invention may be used for rapid bedside evaluation of renal function and also to monitor the efficiency of hemodialysis. The invention is further demonstrated by the following examples. Since many modifications, variations, and changes in detail may be made to the described embodiments, it is intended that all matter in the foregoing description and shown in the accompanying drawings be interpreted as illustrative and not in a limiting sense.

EXAMPLE 1

Synthesis of Indole Disulfonate (FIG. 1, Compound 5, $Y_7=SO_3^-$; $X_7=H$: n=1)

A mixture of 3-methyl-2-butanone (25.2 mL), and p-hydrazinobenzenesulfonic acid (15 g) in acetic acid (45 mL) was heated at 110° C. for 3 hours. After reaction, the mixture was allowed to cool to room temperature and ethyl acetate (100 mL) was added to precipitate the product, which was filtered and washed with ethyl acetate (100 mL). The intermediate compound, 2,3,3-trimethylindolenium-5-sulfonate (FIG. 1, compound 3) was obtained as a pink powder in 80% yield. A portion of compound 3 (9.2 g) in methanol (115 mL) was carefully added to a solution of KOH in isopropanol (100 mL). A yellow potassium salt of the sulfonate was obtained in 85% yield after vacuum-drying for 12 hours. A portion of the 2,3,3-trimethylindolenium-5-sulfonate potassium salt (4 g) and 1,3-propanesultone (2.1 g) was heated in dichlorobenzene (40 mL) at 110° C. for 12 hours. The mixture was allowed to cool to room temperature and the resulting precipitate was filtered and washed with isopropanol. The resulting pink powder was dried under vacuum to give 97% of the desired compound.

Other compounds prepared by a similar method described above include polyhydroxyl indoles such as

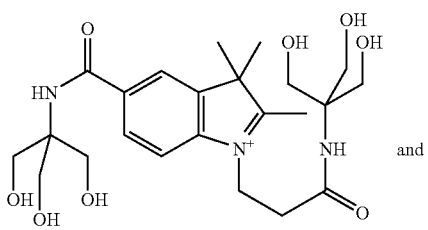

and

-continued

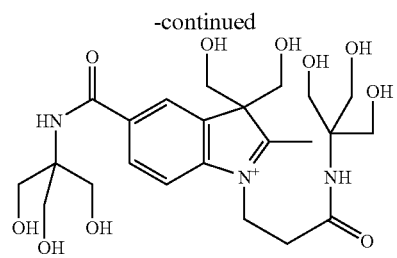

EXAMPLE 2

Synthesis of Indole Disulfonate (FIG. 1, Compound 5, $Y_7=SO_3^-$: $X_7=H$; n=2)

This compound was prepared by the same procedure described in Example 1, except that 1,4-butanesultone was used in place of 1,3-propanesultone.

EXAMPLE 3

Synthesis of Benzoindole Disulfonate (FIG. 2, Compound 8, $Y_7$, $Y_8=SO_3^-$; $X_7=H$; n=2)

This compound was prepared by the same procedure described in Example 1, except that hydrazinonaphthalenedisulfonic acid was used in place of hydrazinobenzenesulfonic acid.

Other compounds prepared by a similar method include polyhydroxyindoles such as:

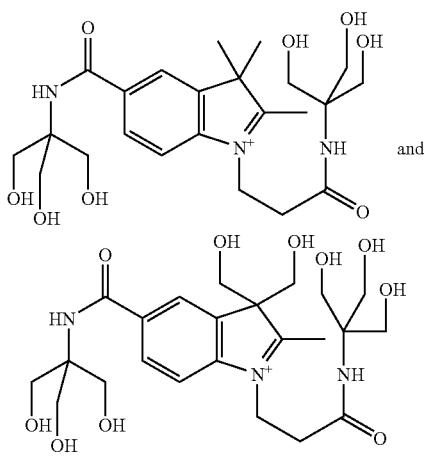

EXAMPLE 4

Synthesis of Benzoindole Disulfonate (FIG. 2, Compound 8, $Y_7$, $Y_8=SO_3^-$; $X_7=OH$: n=4)

This compound was prepared by the same procedure described in Example 1, except that 3-hydroxymethyl-4-hydroxyl-2-butanone was used in place of 3-methyl-2-butanone.

EXAMPLE 5

Synthesis of Bis(ethylcarboxymethyl)indocyanine Dye

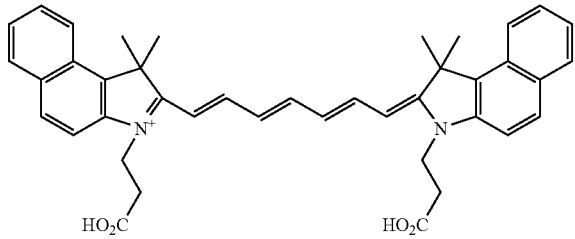

A mixture of 1,1,2-trimethyl-[1H]-benz[e]indole (9.1 g, 43.58 mmoles) and 3-bromopropanoic acid (10.0 g, 65.37 mmoles) in 1,2-dichlorobenzene (40 mL) was heated at 110° C. for 12 hours. The solution was cooled to room temperature and the red residue obtained was filtered and washed with acetonitrile: diethyl ether (1:1) mixture. The solid obtained was dried under vacuum to give 10 g (64%) of light brown powder. A portion of this solid (6.0 g; 16.56 mmoles), glutaconaldehyde dianil monohydrochloride (2.36 g, 8.28 mmoles) and sodium acetate trihydrate (2.93 g, 21.53 mmoles) in ethanol (150 mL) were refluxed for 90 minutes. After evaporating the solvent, 40 mL of 2 N aqueous HCl was added to the residue and the mixture was centrifuged and the supernatant was decanted. This procedure was repeated until the supernatant became nearly colorless. About 5 mL of water:acetonitrile (3:2) mixture was added to the solid residue and lyophilized to obtain 2 g of dark green flakes. The purity of the compound was established with $^1$H-NMR and liquid chromatography/mass spectrometry (LC/MS).

EXAMPLE 6

Synthesis of Bis(pentylcarboxymethyl)indocyanine Dye

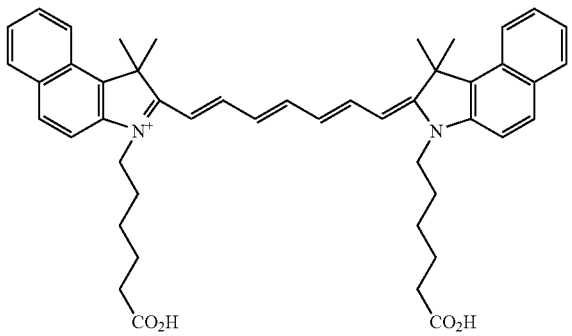

A mixture of 2,2,3-trimethyl-[1H]-benz[e]indole (20 g, 95.6 mmoles) and 6-bromohexanoic acid (28.1 g, 144.1 mmoles) in 1,2-dichlorobenzene (250 mL) was heated at 110° C. for 12 hours. The green solution was cooled to room temperature and the brown solid precipitate formed was collected by filtration. After washing the solid with 1,2-dichlorobenzene and diethyl ether, the brown powder obtained (24 g, 64%) was dried under vacuum at room temperature. A portion of this solid (4.0 g; 9.8 mmoles), glutaconaldehyde dianil monohydrochloride (1.4 g, 5 mmoles) and sodium acetate trihydrate (1.8 g, 12.9 mmoles) in ethanol (80 mL) were refluxed for 1 hour. After evaporating the solvent, 20 mL of a 2 N aqueous HCl was added to the residue and the mixture was centrifuged and the supernatant was decanted. This procedure was repeated until the supernatant became nearly colorless. About 5 mL of water:acetonitrile (3:2) mixture was added to the solid residue and lyophilized to obtain about 2 g of dark green flakes. The purity of the compound was established with $^1$H-NMR, HPLC, and LC-MS.

EXAMPLE 7

Synthesis of polyhydroxyindole sulfonate (FIG. 3. Compound 13, $Y_7$, $Y_8$=$O_3^-$; $X_7$=OH: n=2)

Phosphorus oxychloride (37 ml, 0.4 mole) was added dropwise with stirring to a cooled (−2° C.) mixture of dimethylformamide (DMF, 0.5 mole, 40 mL) and dichloromethane (DCM, 40 mL), followed by the addition of acetone (5.8 g, 0.1 mole). The ice bath was removed and the solution refluxed for 3 hours. After cooling to room temperature, the product was either partitioned in water/DCM, separated and dried, or was purified by fractional distillation. Nuclear magnetic resonance and mass spectral analyses showed that the desired intermediate, 10, was obtained. Reaction of the intermediate with 2 equivalents of 2,2,3-trimethyl-[H]-benz[e]indolesulfonate-N-propanoic acid and 2 equivalents of sodium acetate trihydrate in ethanol gave a blue-green solution after 1.5 hours at reflux. Further functionalization of the dye with bis(isopropylidene)acetal protected monosaccharide is effected by the method described in the literature (J. H. Flanagan, C. V. Owens, S. E. Romero, et al., *Near infrared heavy-atom-modified fluorescent dyes for base-calling in DNA-sequencing application using temporal discrimination. Anal. Chem.*, 1998, 70(13), 2676–2684).

EXAMPLE 8

Figure 4:
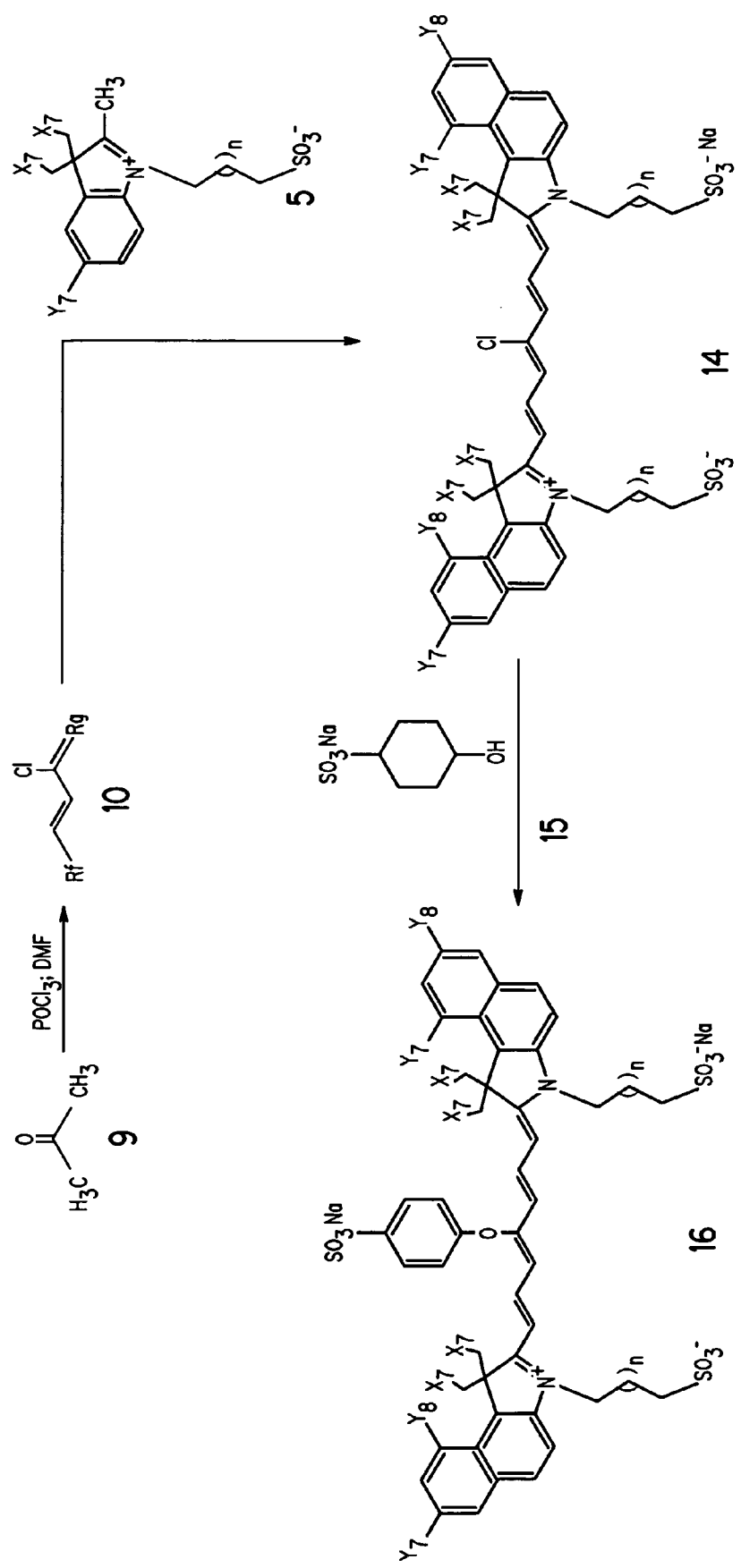
FIG. 4: Reaction pathway for the preparation of benzoindocarbocyanine derivatives.

Synthesis of polyhydroxyindole sulfonate (FIG. 4. Compound 16, $Y_7$, $Y_8$=$SO_3^-$: $X_7$—H; n=1)

Preparation of this compound was readily accomplished by the same procedure described in Example 6 using p-hydroxybenzenesulfonic acid in the place of the monosaccharide, and benzoindole instead of indole derivatives.

EXAMPLE 9

Figure 5:
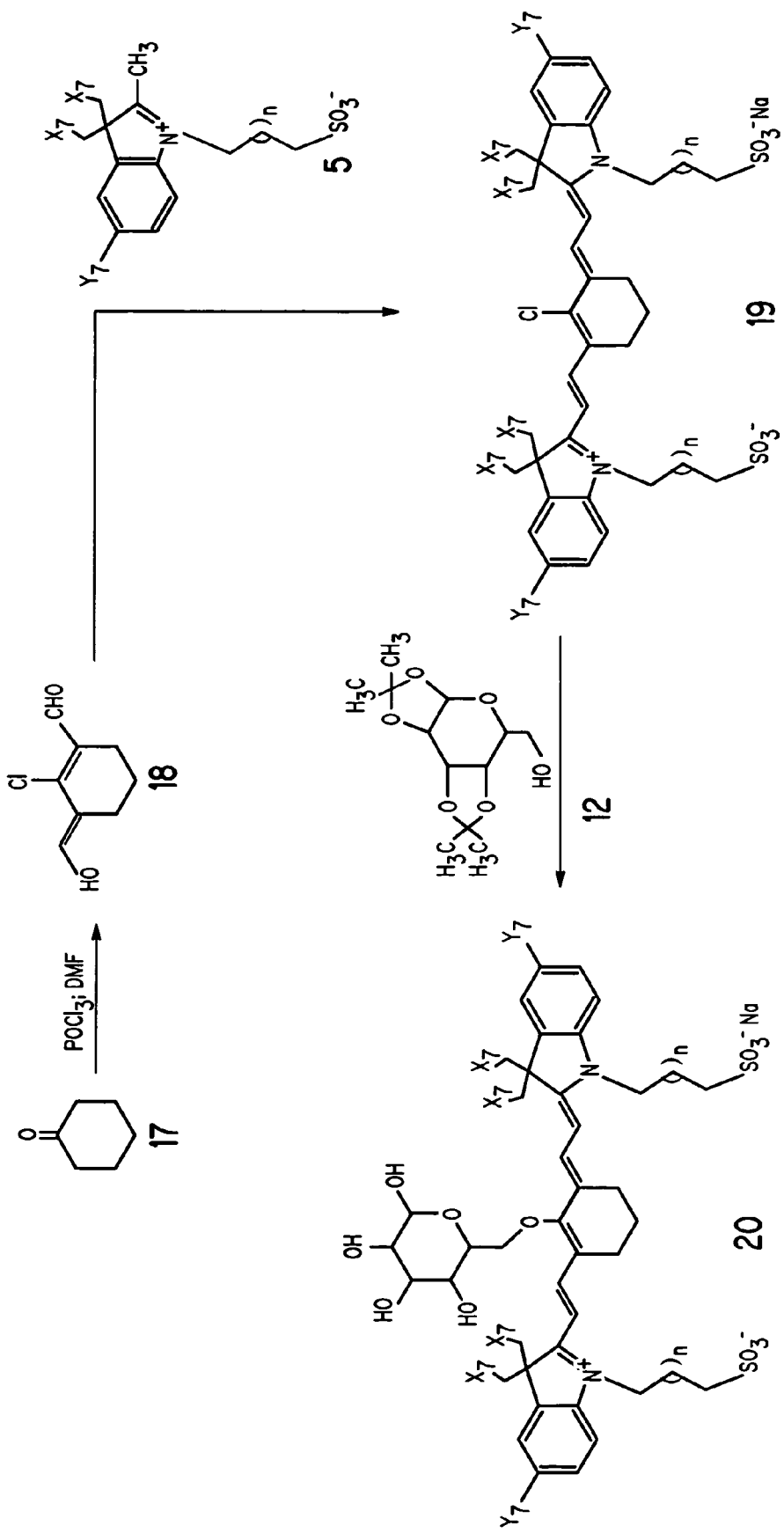
FIG. 5: Reaction pathway for the preparation of robust indocarbocyanine derivatives.

Synthesis of polyhydroxyindole Sulfonate (FIG. 5. Compound 20, $Y_7$, $Y_8$=H; $X_7$=OH: n=1)

The hydroxyindole compound was readily prepared by a literature method (P. L. Southwick, J. G. Cairns, L. A. Ernst, and A. S. Waggoner, *One pot Fischer synthesis of (2,3,3-trimethyl-3-H-indol-5-yl)-acetic acid derivatives as intermediates for fluorescent biolabels, Org. Prep. Proced. Int. Briefs*, 1988, 20(3), 279–284). Reaction of p-carboxymethylphenylhydrazine hydrochloride (30 mmol, 1 equiv.) and 1,1-bis(hydroxymethyl)propanone (45 mmol, 1.5 equiv.) in acetic acid (50 mL) at room temperature for 30 minutes and at reflux for 1 gave (3,3-dihydroxymethyl2-methyl-3-H-indol-5-yl)-acetic acid as a solid residue.

The intermediate 2-chloro-1-formyl-3-hydroxymethylenecyclo-hexane was prepared as described in the literature (G. A. Reynolds and K. H. Drexhage, Stable heptamethine pyrylium dyes that absorb in the infrared. *J. Org. Chem.*, 1977, 42(5), 885–888). Equal volumes (40 mL each) of dimethylformamide (DMF) and dichloromethane were mixed and the solution was cooled to −10° C. in acetone-dry ice bath. Under argon atmosphere, phosphorus oxychloride (40 mL) in dichloromethane was added dropwise to the cool DMF solution, followed by the addition of 10 g of cyclohexanone. The resulting solution was allowed to warm up to room temperature and heated at reflux for 6 hours. After cooling to room temperature, the mixture was poured into ice-cold water and stored at 4° C. for 12 hours. A yellow powder was obtained. Condensation of a portion of this cyclic dialdehyde (1 equivalent) with the indole intermediate (2 equivalents) was carried out as described in Example 5. Further, the functionalization of the dye with bis (isopropylidene)acetal protected monosaccharide was effected by the method described in the literature (J. H. Flanagan, C. V. Owens, S. E. Romero, et al., *Near infrared heavy-atom-modified fluorescent dyes for base-calling in DNA-sequencing application using temporal discrimination. Anal. Chem.*, 1998, 70(13), 2676–2684).

EXAMPLE 10

Figure 6:
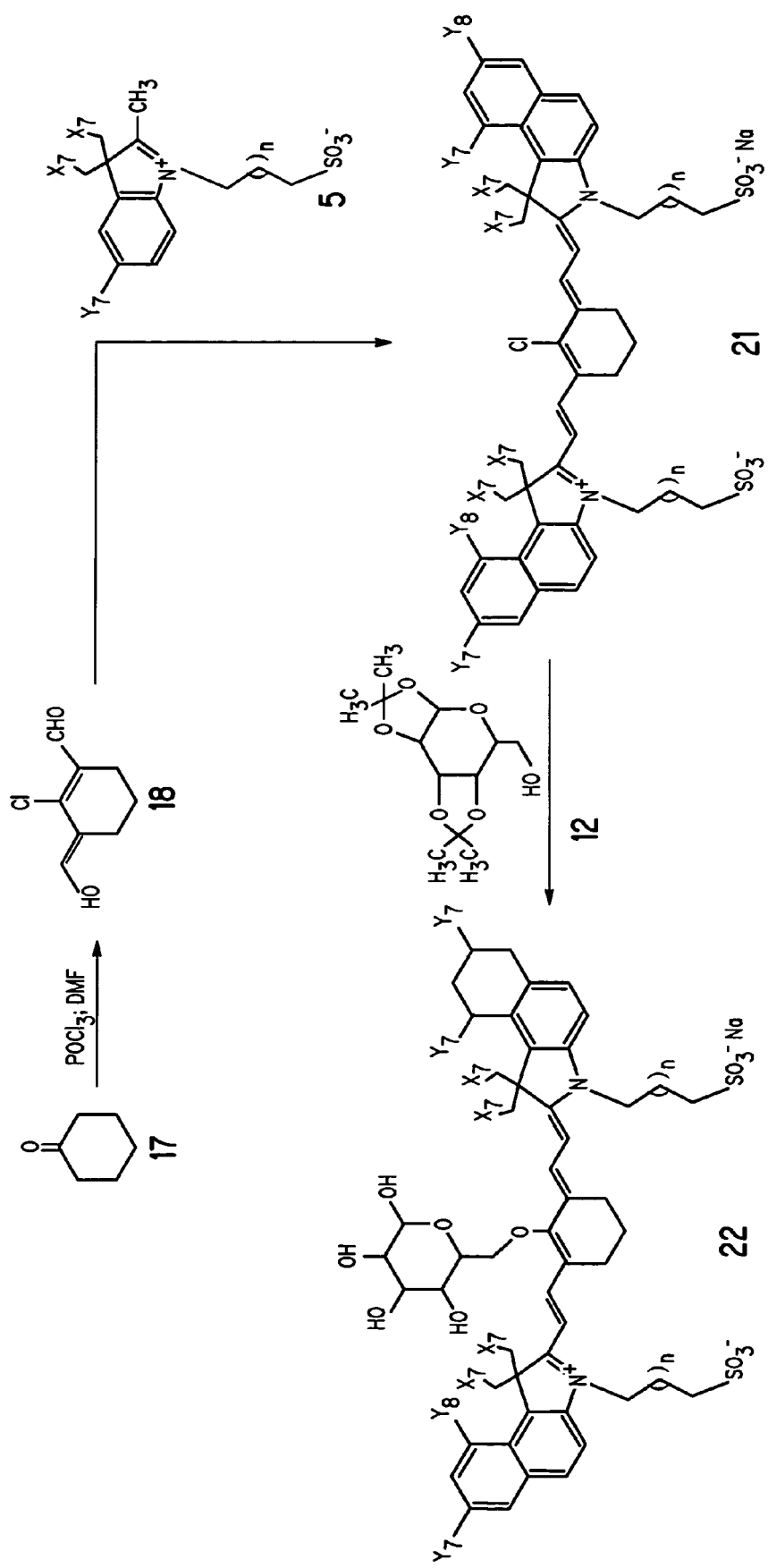
FIG. 6: Reaction pathway for the preparation of robust benzoindocarbocyanine derivatives.

Synthesis of polyhydroxylbenzoindole Sulfonate
(FIG. 6. Compound 22, $Y_7$, $Y_8$=H; $X_7$=OH; n=1)

A similar method described in Example 8 was used to prepare this compound by replacing the indole with benzoindole derivatives.

EXAMPLE 11

Figure 7:
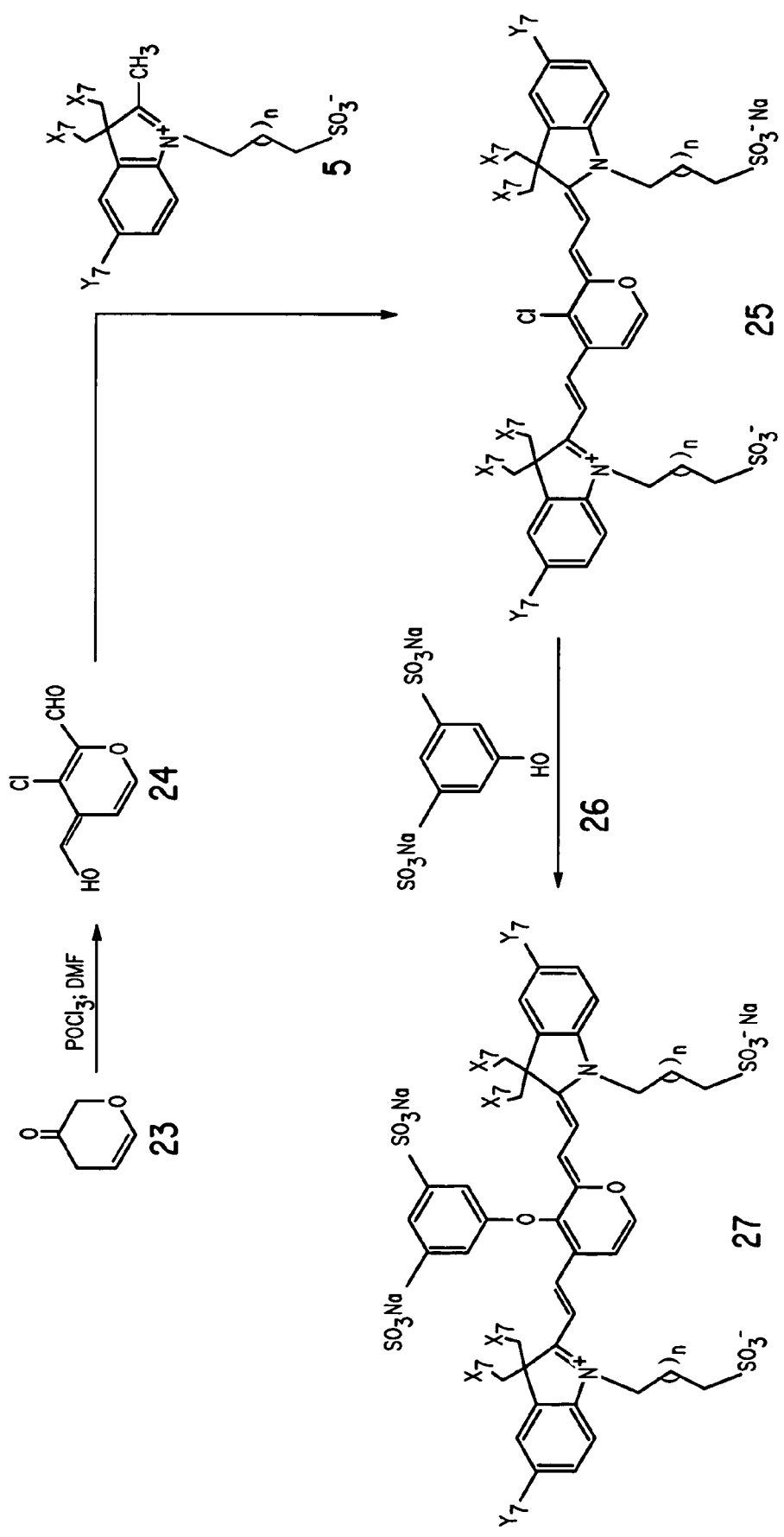
FIG. 7: Reaction pathway for the preparation of long-wavelength absorbing indocarbocyanine derivatives.
Figure 8A:
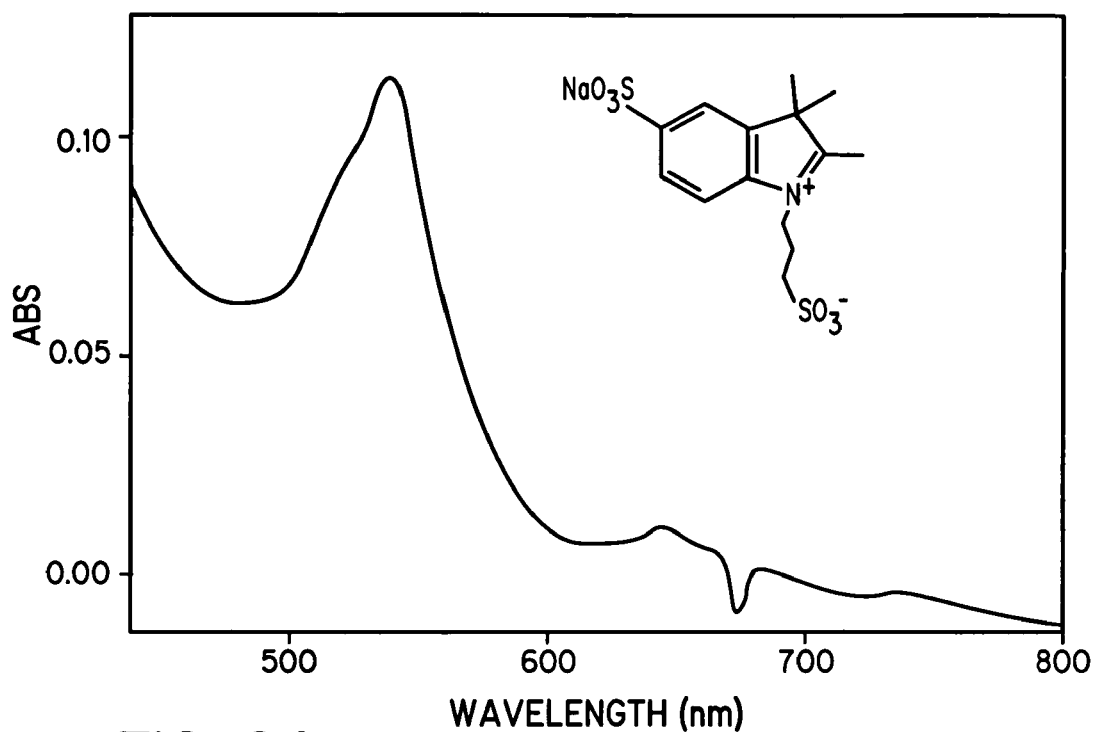
FIG. 8A: Absorption spectrum of indoledisulfonate in water.
Figure 8B:
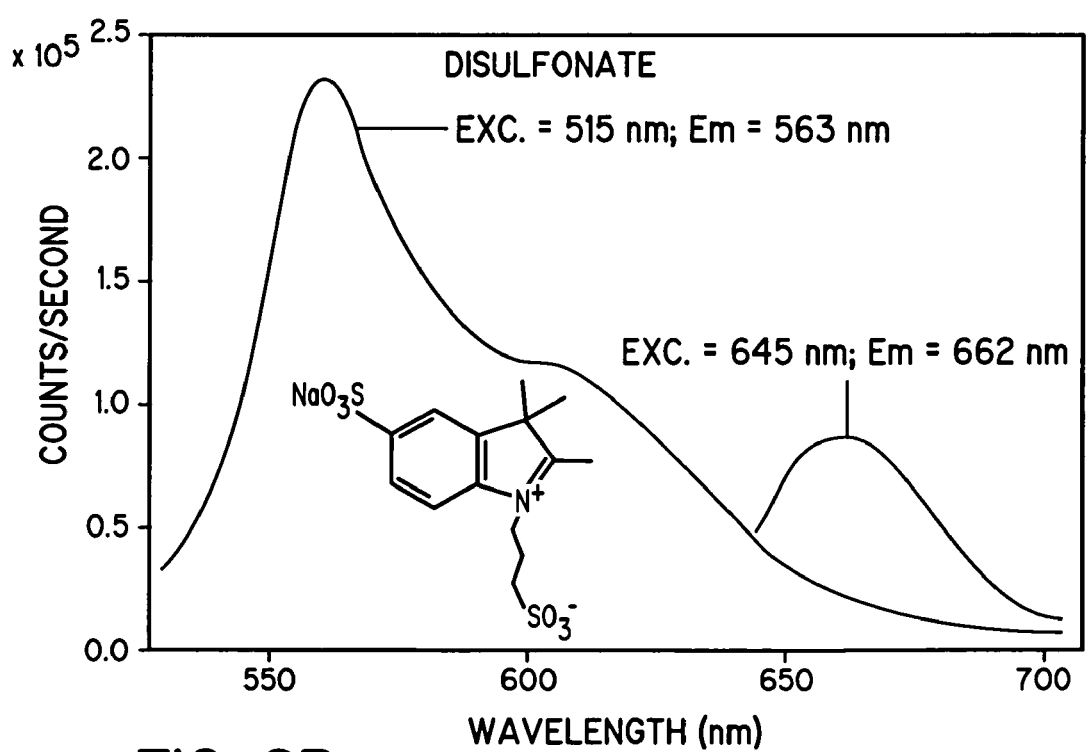
FIG. 8B: Emission spectrum of indoledisulfonate in water.
Figure 9A:
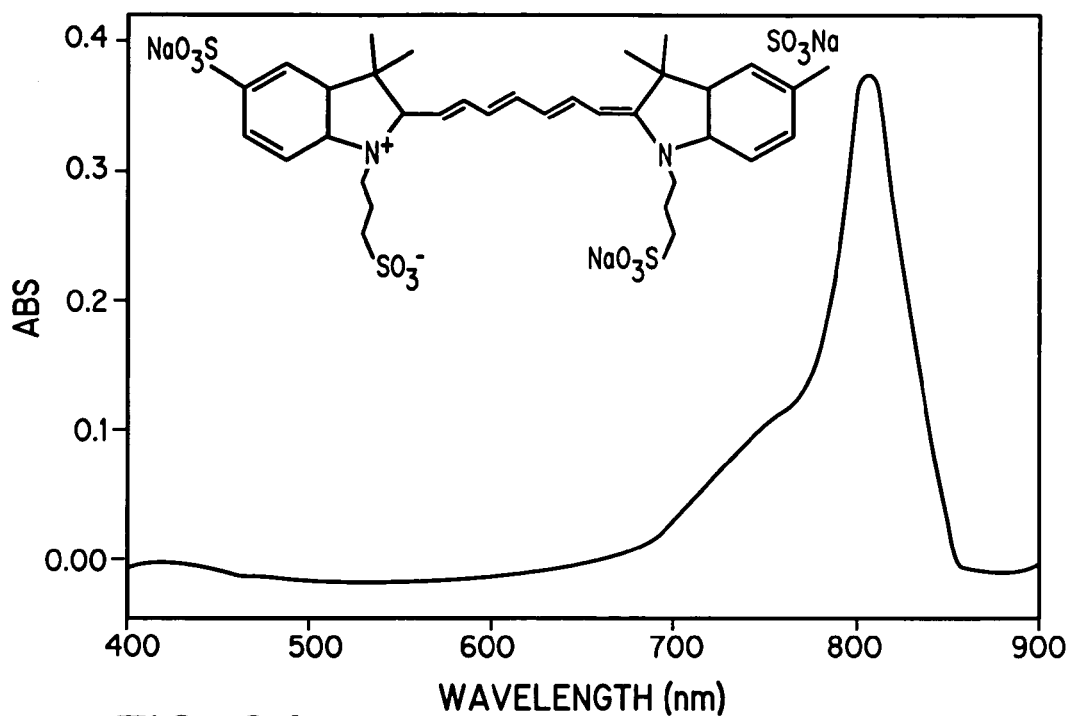
FIG. 9A: Absorption spectrum of indocarbocyaninetetrasulfonate in water.
Figure 9B:
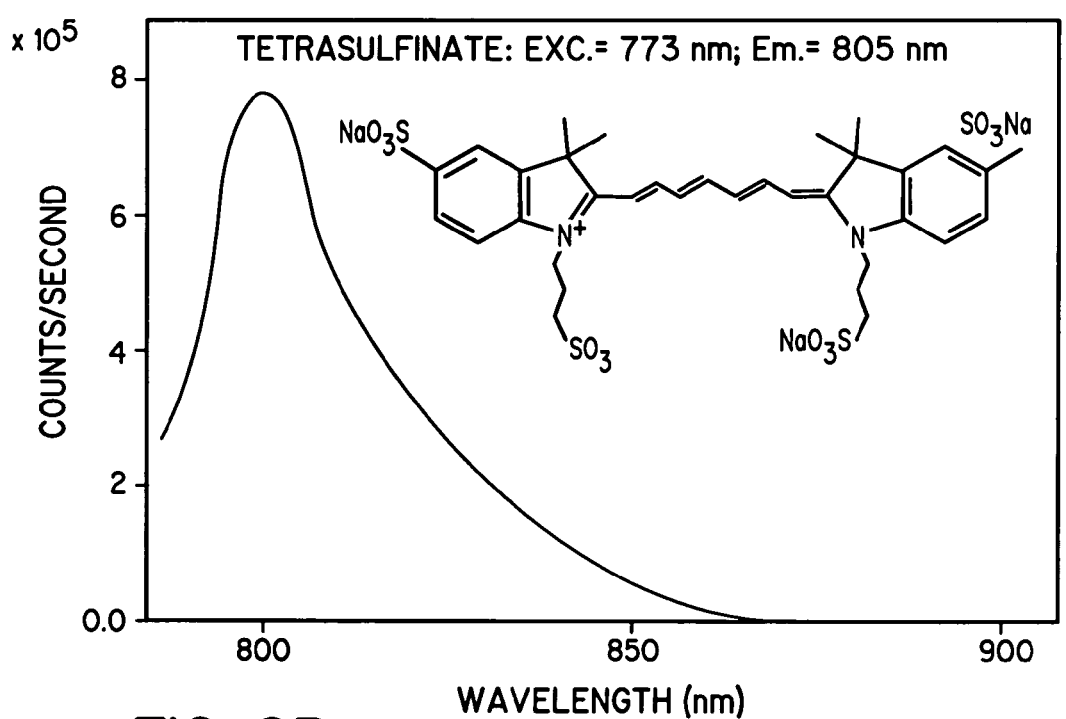
FIG. 9B: Emission spectrum of indocarbocyaninetetrasulfonate in water.
Figure 10A:
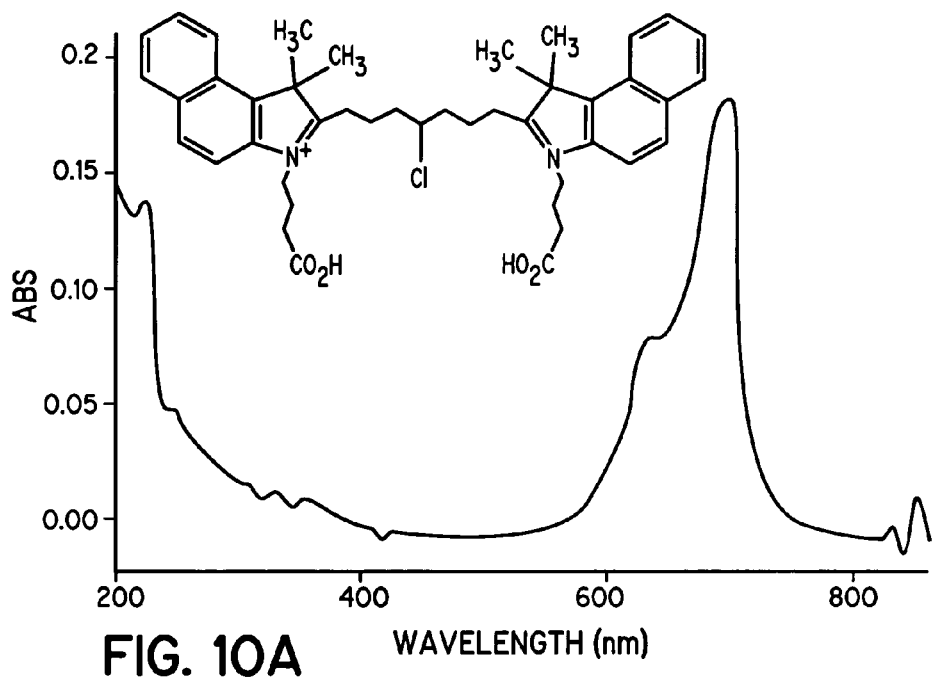
FIG. 10A: Absorption spectrum of chloroindocarbocyanine in acetonitrile.
Figure 10B:
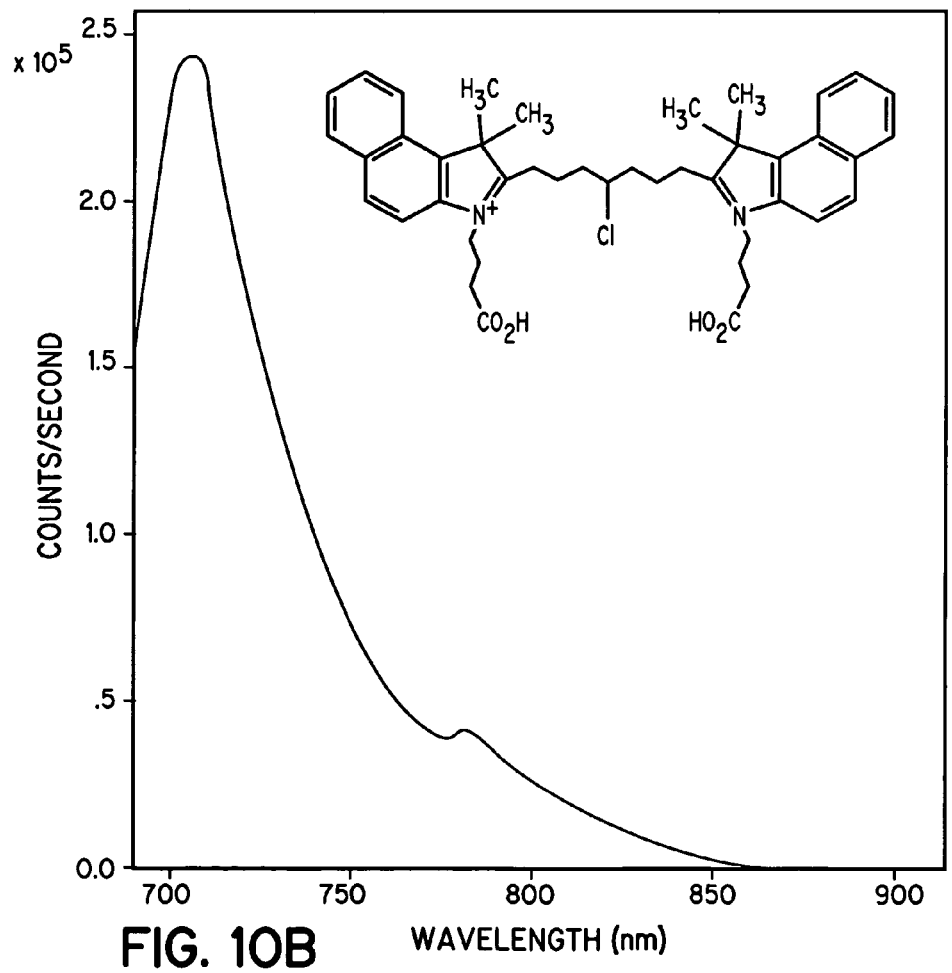
FIG. 10B: Emission spectrum of chloroindocarbocyanine in acetonitrile.
Figure 11:
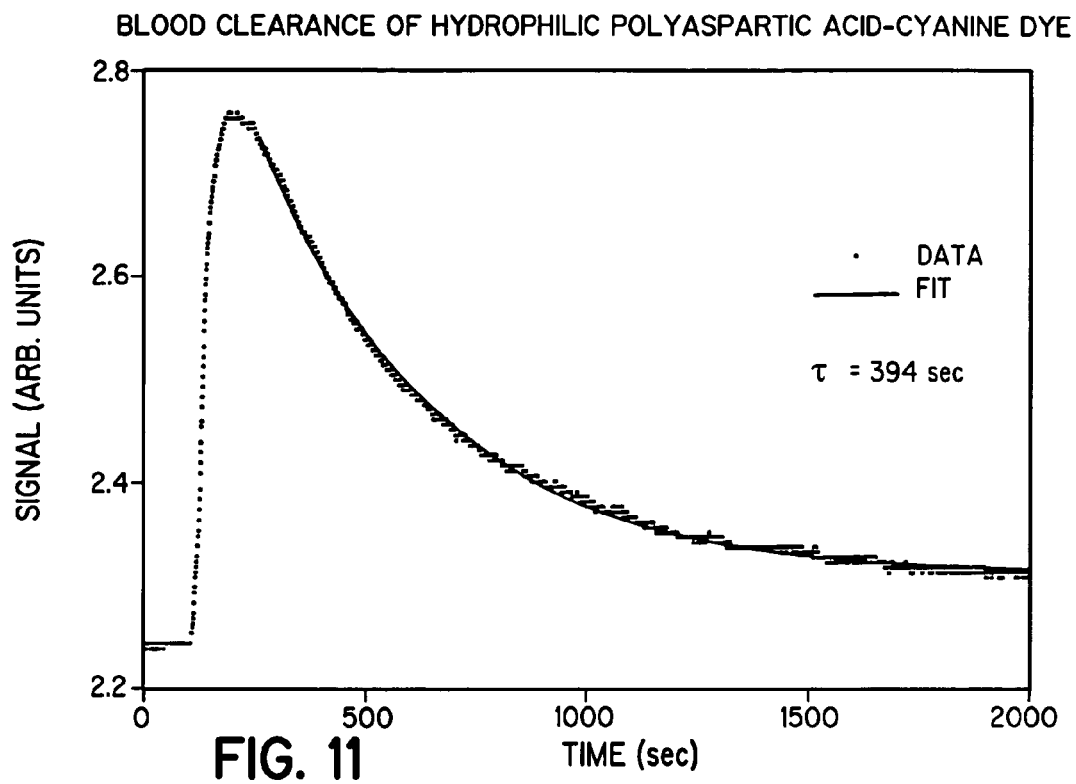
FIG. 11: Blood clearance profile of carbocyanine-polyaspartic (10 kDa) acid conjugate in a rat.
Figure 12:
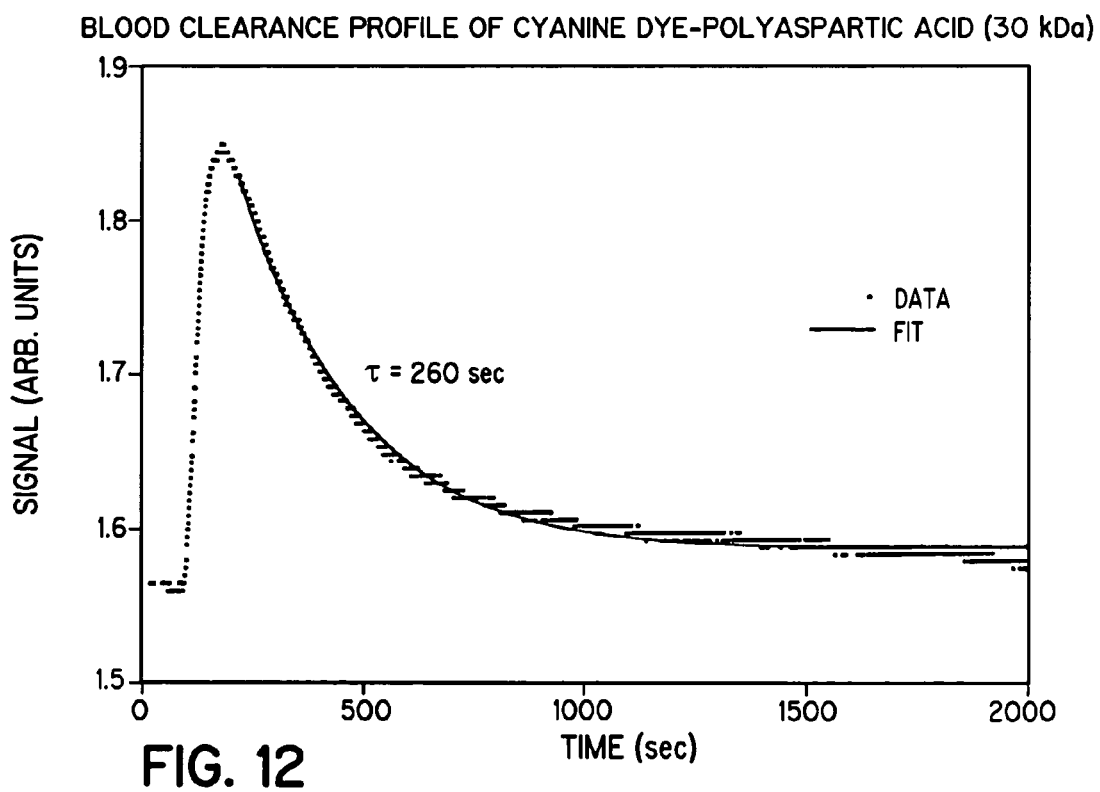
FIG. 12: Blood clearance profile of carbocyanine-polyaspartic (30 kDa) acid conjugate in a rat.
Figure 13:
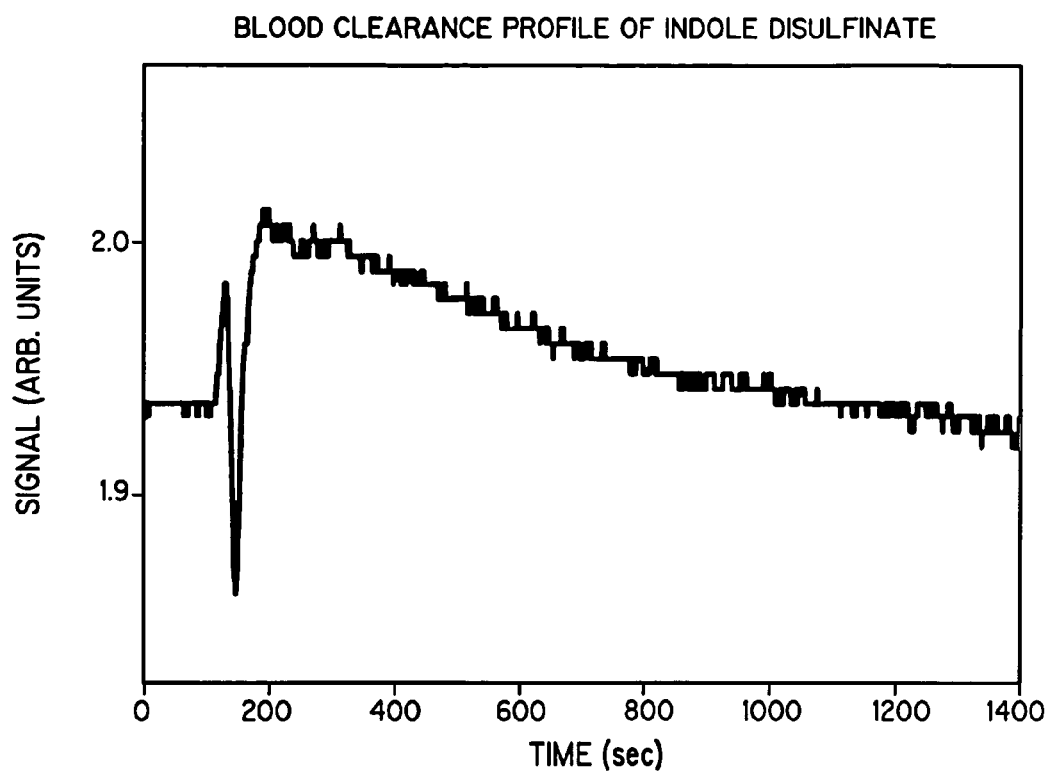
FIG. 13: Blood clearance profile of indoledisulfonate in a rat.
Figure 14:
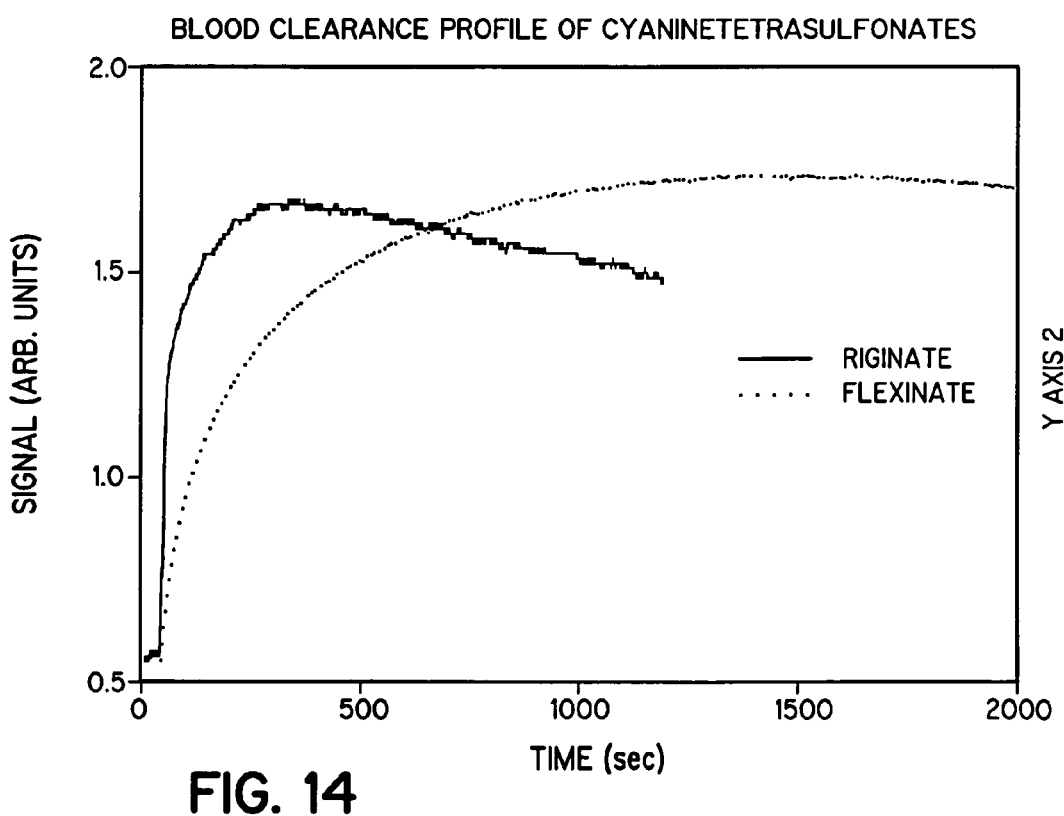
FIG. 14: Blood clearance profile of carbocyaninetetrasulfonates in a rat.

Synthesis of Rigid Heteroatomic Indole Sulfonate
(FIG. 7. Compound 27, $Y_7$, $Y_8$, $X_7$=H; n=1)

Starting with 3-oxo-4-cyclohexenone, this heteroatomic hydrophilic dye was readily prepared as described in Example 8.

EXAMPLE 12

Minimally Invasive Monitoring of the Blood Clearance Profile of the Dyes

A laser of appropriate wavelength for excitation of the dye chromophore was directed into one end of a fiber optic bundle and the other end was positioned a few millimeters from the ear of a rat. A second fiber optic bundle was also positioned near the same ear to detect the emitted fluorescent light, and the other end was directed into the optics and electronics for data collection. An interference filter (IF) in the collection optics train was used to select emitted fluorescent light of the appropriate wavelength for the dye chromophore.

Sprague-Dawley or Fischer 344 rats were anesthetized with urethane administered via intraperitoneal injection at a dose of 1.35 g/kg body weight. After the animals had achieved the desired plane of anesthesia, a 21 gauge butterfly with 12" tubing was placed in the lateral tail vein of each animal and flushed with heparinized saline. The animals were placed onto a heating pad and kept warm throughout the entire study. The lobe of the left ear was affixed to a glass microscope slide to reduce movement and vibration.

Incident laser light delivered from the fiber optic was centered on the affixed ear. Data acquisition was then initiated, and a background reading of fluorescence was obtained prior to administration of the test agent.

The compound was administered to the animal through a bolus injection in the lateral tail vein. The dose was typically 0.05 to 20 µmole/kg of body weight. The fluorescence signal rapidly increased to a peak value, then decayed as a function of time as the conjugate cleared from the bloodstream.

This procedure was repeated with several dye-peptide conjugates in normal and tumored rats. Representative profiles are shown in FIGS. 6–10.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A pharmaceutical composition comprising an effective amount of the compound of formula 4

Formula 4

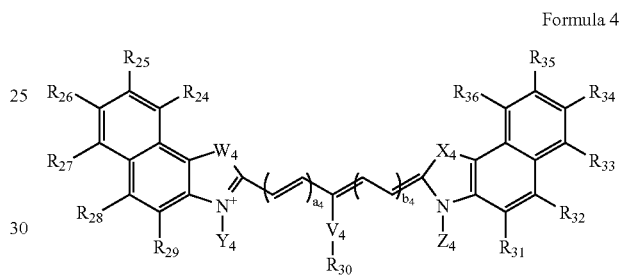

for a diagnostic or therapeutic procedure and a pharmaceutically acceptable carrier for administration to a mammal wherein at least one of $W_4$ and $X_4$ is S and the other is selected from the group consisting of —$CR_cR_d$—, —$NR_c$—, —O—, and —S—; $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$ and $R_{36}$, $Y_4$, and $Z_4$ are independently selected from the group consisting of C1–C10 alkoxyl, C1–C10 polyalkoxyalkyl, C1–C20 polyhydroxyalkyl, C5–C20 polyhydroxyaryl, glucose, saccharides, amino, C1–C10 aminoalkyl, cyano, nitro, halogen, hydrophilic peptides, arylpolysulfonates, C1–C10 alkyl, C5–C20 aryl, —$SO_3T$, —$CO_2T$, —OH, —$(CH_2)_aSO_3T$, —$(CH_2)_aOSO_3T$, —$(CH_2)_aNHSO_3T$, —$(CH_2)_aCO_2(CH_2)_bSO_3T$, —$(CH_2)_aOCO(CH_2)_bSO_3T$, —$(CH_2)_aCONH(CH_2)_bSO_3T$, —$(CH_2)_aNHCO(CH_2)_bSO_3T$, —$(CH_2)_aNHCONH(CH_2)_bSO_3T$, —$(CH_2)_aNHCSNH(CH_2)_bSO_3T$, —$(CH_2)_aOCONH(CH_2)_bSO_3T$, —$(CH_2)_aPO_3HT$, —$(CH_2)_aPO_3T_2$, —$(CH_2)_aOPO_3HT$, —$(CH_2)_aOPO_3T_2$, —$(CH_2)_aNHPO_3HT$, —$(CH_2)_a$ $NHPO_3T_2$, —$(CH_2)_aCO_2(CH_2)_bPO_3HT$, —$(CH_2)_a$ $CO_2(CH_2)_bPO_3T_2$, —$(CH_2)_aOCO(CH_2)_bPO_3HT$, —$(CH_2)_a$ $OCO(CH_2)_bPO_3T_2$, —$(CH_2)_aCONH(CH_2)_b$ $PO_3HT$, —$(CH_2)_aCONH(CH_2)_bPO_3T_2$, —$(CH_2)_aNHCO$ $(CH_2)_b$ $PO_3HT$, —$(CH_2)_aNHCO(CH_2)_bPO_3T_2$, —$(CH_2)_aN$-$HCONH(CH_2)_bPO_3HT$, —$(CH_2)_aNHCONH(CH_2)_bPO_3T_2$, —$(CH_2)_aNHCSNH(CH_2)_bPO_3HT$, —$(CH_2)_aNHCSNH$ $(CH_2)_bPO_3T_2$, —$(CH_2)_aOCONH(CH_2)_bPO_3HT$, and —$(CH_2)_aOCONH(CH_2)_bPO_3T_2$, —$CH_2(CH_2—O—CH_2)_c$—$CH_2$—OH, —$(CH_2)_d$—$CO_2T$, —$CH_2$—$(CH_2$—O—$CH_2)_e$—$CH_2$—$CO_2T$, —$(CH_2)_f$—$NH_2$, —$CH_2$—$(CH_2$—O—$CH_2)_9$—$CH_2$—$NH_2$, —$(CH_2)_h$—$N(R_a)$ —$(CH_2)_i$—$CO_2T$, and —$(CH_2)_j$—$N(R_b)$ —$CH_2$—$(CH_2$—O—$CH_2)_k$—$CH_2$—$CO_2T$; $V_4$ is a single bond or is selected from the group consisting of —O—, —S—, —Se—, and —$NR_a$; $a_4$ and $b_4$ vary from 0 to 5; a, b, d, f, h, i, and j independently vary from 1–10; c, e, g, and k independently vary from 1–100; $R_a$, $R_b$, $R_c$, and $R_d$ are defined in the same manner as $Y_4$; and T is either H or a negative charge.

2. The composition as in claim 1 further comprising a contrast agent.

3. The composition as in claim 1 wherein the compound comprises a radioactive halogen.

4. The composition as in claim 1 wherein at least one R group of the compound is replaced by a polyamino carboxylic acid.

5. The composition of claim 4 further comprising a radioactive metal ion or a paramagnetic metal ion.

6. The composition as in claim 1, 3, or 4 formulated as at least one of a liposome, a micell, a microcapsule, or a microparticle.

7. The composition as in claims 1, 3, or 4 formulated as at least one of iron oxide particles, silver particles, or gold particles.

8. A method for performing therapy or diagnostic imaging comprising administering to a mammal an effective amount of the compound of formula 4

Formula 4

[Chemical structure with substituents $R_{24}$–$R_{36}$, $W_4$, $X_4$, $Y_4$, $Z_4$, $V_4$, $a_4$, $b_4$]

wherein at least one of $W_4$ and $X_4$ is S and the other is selected from the group consisting of —$CR_cR_d$, —$NR_c$, —O—, and —S—; $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$ and $R_{36}$, $Y_4$, and $Z_4$ are independently selected from the group consisting of C1–C10 alkoxyl, C1–C10 polyalkoxyalkyl, C1–C20 polyhydroxyalkyl, C5–C20 polyhydroxyaryl, glucose, saccharides, amino, C1–C10 aminoalkyl, cyano, nitro, halogen, hydrophilic peptides, arylpolysulfonates, C1–C10 alkyl, $C_5$–$C_{20}$ aryl, —$SO_3T$, —$CO_2T$, —OH, —$(CH_2)_aSO_3T$, —$(CH_2)_aOSO_3T$, —$(CH_2)_aNHSO_3T$, —$(CH_2)_aCO_2(CH_2)_bSO_3T$, —$(CH_2)_aOCO(CH_2)_bSO_3T$, —$(CH_2)_aCONH(CH_2)_bSO_3T$, —$(CH_2)_aNHCO(CH_2)_bSO_3T$, —$(CH_2)_aNHCONH(CH_2)_bSO_3T$, —$(CH_2)_aNHCSNH(CH_2)_bSO_3T$, —$(CH_2)_aOCONH(CH_2)_bSO_3T$, —$(CH_2)_aPO_3HT$, —$(CH_2)_aPO_3T_2$, —$(CH_2)_aOPO_3HT$, —$(CH_2)_aOPO_3T_2$, —$(CH_2)_aNHPO_3HT$, —$(CH_2)_a$ N $HPO_3T_2$, —$(CH_2)_aCO_2(CH_2)_bPO_3HT$, —$(CH_2)_a$ $CO_2(CH_2)_bPO_3T_2$, —$(CH_2)_aOCO(CH_2)_bPO_3HT$, —$(CH_2)_a$ $OCO(CH_2)_bPO_3T_2$, —$(CH_2)_aCONH(CH_2)_bPO_3HT$, —$(CH_2)_aCONH(CH_2)_bPO_3T_2$, —$(CH_2)_aNHCO(CH_2)_bPO_3HT$, —$(CH_2)_aNHCO(CH_2)_bPO_3T_2$, —$(CH_2)_aNHCONH(CH_2)_bPO_3HT$, —$(CH_2)_aNHCONH(CH_2)_bPO_3T_2$, —$(CH_2)_aNHCSNH(CH_2)_bPO_3HT$, —$(CH_2)_aNHCSNH(CH_2)_bPO_3T_2$, —$(CH_2)_aOCONH(CH_2)_bPO_3HT$, and —$(CH_2)_aOCONH(CH_2)_bPO_3T_2$, —$CH_2(CH_2$—O—$CH_2)_c$—$CH_2$—OH, —$(CH_2)_d$—$CO_2T$, —$CH_2$—$(CH_2$—O—$CH_2)_e$—$CH_2$—$CO_2T$, —$(CH_2)_f$—$NH_2$, —$CH_2$—$(CH_2$—O—$CH_2)_g$—$CH_2$—$NH_2$, —$(CH_2)_h$—$N(R_a)$—$(CH_2)_i$—$CO_2T$, and —$(CH_2)_j$—$N(R_b)$ —$CH_2$—$(CH_2$—O—$CH_2)_k$—$CH_2$—$CO_2T$; $V_4$ is a single bond or is selected from the group consisting of —O—, —S—, —Se—, and —$NR_a$, $a_4$ and $b_4$ vary from 0 to 5; a, b, d, f, h, i, and j independently vary from 1–10; c, e, g, and k independently vary from 1–100; $R_a$, $R_b$, $R_c$, and $R_d$ are defined in the same manner as $Y_4$; and T is either H or a negative charge, and thereafter performing the diagnostic or therapeutic procedure.

9. The method as in claim 8 wherein said therapy or diagnostic imaging utilizes light of wavelength in the region of 350–1300 nm.

10. The method of claim 9 wherein said therapy or diagnostic imaging comprises monitoring a blood clearance profile by fluorescence using light of wavelength in the region of 350 nm to 1300 nm.

11. The method as in claim 8 wherein said therapy or diagnostic imaging comprises monitoring a blood clearance profile by absorption using light of wavelength in the region of 350 nm to 1300 nm.

12. The method as in claim 8 wherein the compound contains a radioactive halogen and imaging the mammal by at least one of optical imaging and nuclear imaging.

13. The method as in claim 8 where the compound administered has at least one R group replaced by a polyamino carboxylic acid.

14. The method as in claim 8 wherein the compound administered further comprises a radioactive metal ion or a paramagnetic metal ion.

15. The method as in claim 13 or 14 further comprising imaging by at least one of optical imaging, nuclear imaging, or magnetic resonance imaging.

16. The method as in claim 8 or 13 wherein the compound is administered in a formulation selected from at least one of liposomes, micelles, microcapsules, or microparticles.

17. The method as in claim 8, 12, 13, or 14 wherein the compound is administered in a formulation selected from at least one of iron oxide particles, silver particles, or gold particles.

18. The method as in claim 8, 12, 13, or 14 further comprising administering a non-optical contrast agent and imaging by at least one of magnetic resonance, ultrasound, x-ray, positron emission tomography, computed tomography, optoacoustic imaging, and single photon emission computed tomography.

19. The method as in claim 8, 12, 13, or 14 wherein said procedure is for physiological function monitoring.

20. The method as in claim 8, 12, 13, or 14 wherein said therapy or diagnostic imaging is for at least one of renal function monitoring, cardiac function monitoring, and kidney function monitoring.

21. The method as in claim 8, 12, 13, or 14 wherein said therapy or diagnostic imaging is for determining organ perfusion in vivo.

22. The method as in claim 8, 12, 13, or 14 further comprising optically imaging the mammal.

23. A method of therapy or diagnostic imaging a patient comprising administering a non-optical contrast agent composition further comprising the composition as in claim 1, 4, or 5 and performing at least one of therapy or diagnostic imaging.

24. The method of claim 23 wherein the non-optical contrast agent composition is selected from a magnetic resonance composition, a computed tomography composition, an x-ray composition, a nuclear imaging composition, a positron emission tomography composition, a single photon emission computed tomography composition, an optoacoustic imaging composition and an ultrasound composition.

25. The method of claim 23 wherein the compound stabilizes or buffers the non-optical contrast agent composition.

* * * * *

UNITED STATES PATENT AND TRADEMARK OFFICE
CERTIFICATE OF CORRECTION

PATENT NO. : 7,175,831 B2  Page 1 of 3
APPLICATION NO. : 10/751232
DATED : February 13, 2007
INVENTOR(S) : Achilefu et al.

It is certified that error appears in the above-identified patent and that said Letters Patent is hereby corrected as shown below:

Title Page, item [56], column 2, under U.S. PATENT DOCUMENTS, "6,083,486 A 7/2000 Licha et al." should be deleted.

IN COLUMN 3
In column 3, line 12, "of techentium" should read --of technetium--.
In column 3, line 12, "and $99^{m}$TcN0-" should read --and $^{99m}$TcN0- --.
In column 3, line 18, "sulfonate)]3H$_2$O," should read --sulfonate)]-3H$_2$O,--.

IN COLUMN 4
In column 4, line 14, "wherein $R_3$, R4, $R_5$, $R_6$, and" should read --wherein $R_3$, $R_4$, $R_5$, $R_6$, and--.
In column 4, line 38, "-N($R_b$)" should read -- -N($R_a$)--.

IN COLUMN 5
In column 5, lines 45-46, "-(CH$_2$)$_a$ OCO(CH$_2$ (CH$_2$)$_b$ SO$_3$T" should read -- -(CH$_2$)$_a$ OCO(CH$_2$)$_b$ SO$_3$T--.
In column 5, line 48, "-CH$_2$)$_a$" should read -- -(CH$_2$)$_a$--.

In column 6, line 45, "and X4 are selected" should read --and $X_4$ are selected--.

IN COLUMN 7
In column 7, line 9, "(CH$_2$)$_a$" should read -- -(CH$_2$)$_a$--.
In column 7, line 29, "D5 is a single or a" should read --$D_5$ is a single or a--.
In column 7, line 58, "wherein $R_{46}$, $R_{47}$, $R_{49}$, $R_{49}$" should read --wherein $R_{46}$, $R_{47}$, $R_{48}$, $R_{49}$--.

IN COLUMN 8
In column 8, line 4, "-(Ch$_2$)$_a$" should read -- -(CH$_2$)$_a$--.
In column 8, line 21, "-(Ch$_2$" should read -- -(CH$_2$--.
In column 8, line 22, "-Ch$_2$" should read -- -CH$_2$--.
In column 8, line 25, "D6 is a single or a" should read --$D_6$ is a single or a--.
In column 8, line 26, "A6, $B_6$ and $E_6$" should read --$A_6$, $B_6$ and $E_6$--.

IN COLUMN 10
In column 10, line 20, "-Ch$_2$)$_g$-" should read -- -CH$_2$)$_g$- --.
In column 10, line 22, "-Ch$_2$" should read -- -CH$_2$--.
In column 10, line 24, "a, b, d, f, h, I, and j" should read --a, b, d, f, h, i, and j--.
In column 10, lines 37-38, "-CH$_2$(CH$_2$-C-CH$_2$)C-CH$_2$-OH" should read -- -CH$_2$(CH$_2$-O-CH$_2$)$_c$-CH$_2$-OH--.
In column 10, line 39, "-(CH$_2$)$_r$NH$_2$" should read -- -(CH$_2$)$_f$-NH$_2$--.
In column 10, line 44, "a, b, d, f, h, I, and j" should read --a, b, d, f, h, i, and j--.

UNITED STATES PATENT AND TRADEMARK OFFICE
CERTIFICATE OF CORRECTION

PATENT NO. : 7,175,831 B2
APPLICATION NO. : 10/751232
DATED : February 13, 2007
INVENTOR(S) : Achilefu et al.

It is certified that error appears in the above-identified patent and that said Letters Patent is hereby corrected as shown below:

IN COLUMN 11
In column 11, line 17, "-O-CH$_2$)$_k$" should read --(CH$_2$-O-CH$_2$)$_k$--.
In column 11 line 18, "W$_4$ and X4" should read --W$_4$ and X$_4$--.
In column 11, line 43, "and -NR$_a$D$_5$" should read --and -NR$_a$; D$_5$--.
In column 11, line 64, "S \O$_3$T," should read --SO$_3$T,--.

In column 12, line 8, "A, B$_6$, D$_6$, and E$_6$ may"
should read --A$_6$, B6, D$_6$, and E$_6$ may--.

In column 15, line 32, "X$_7$=H: n=1)" should read --X$_7$=H; n=1)--.

IN COLUMN 16
In column 16, line 17, "SO$_3$$^-$: X$_7$=H; n=2)" should read --SO$_3$$^-$; X$_7$=H; n=2)--.
In column 16, line 61, "X$_7$=OH: n=4)" should read --X$_7$=OH; n=4)--.

IN COLUMN 18
In column 18, line 15, "Y$_8$= O$_3$$^-$; X$_7$=OH: n=2)"
should read --Y$_8$= O$_3$$^-$; X$_7$=OH; n=2)--
In column 18, line 42, "SO$_3$$^-$: X$_7$-H; n=1)" should read --SO$_3$$^-$; X$_7$=H; n=1)--.
In column 18, line 52, "X$_7$=OH: n=1)" should read --X$_7$=OH; n=1)--.
In column 18, line 63, "at reflux for 1 gave" should read --at reflux for 1 hr. gave--.
In column 18, line 63, "dihydroxymethy12-methyl-3-" should read
--dihydroxymethyl-2-methyl-3- --.

In column 19, line 38, "cyclohexenone," should read --cyclohexanone,--.

IN THE CLAIMS
In column 20, line 63, CLAIM 1, "(CH$_2$-O-CH$_2$)$_9$-CH$_2$-NH$_2$" should read
--(CH$_2$-O-CH$_2$)$_g$-CH$_2$-NH$_2$--.

UNITED STATES PATENT AND TRADEMARK OFFICE
CERTIFICATE OF CORRECTION

PATENT NO. : 7,175,831 B2
APPLICATION NO. : 10/751232
DATED : February 13, 2007
INVENTOR(S) : Achilefu et al.

It is certified that error appears in the above-identified patent and that said Letters Patent is hereby corrected as shown below:

IN COLUMN 21
In column 21, lines 4-5, CLAIM 2, "as in claim 1 further comprising a conprising a" should read --as in claim 1 further comprising a--
In column 21, line 16, CLAIM 7, "as in claims 1, 3, or 4" should read --as in claim 1, 3, or 4--.
In column 21, line 40, CLAIM 8, "$C_5$-$C_{20}$ aryl," should read --C5-C20 aryl,--.
In column 21, line 59, CLAIM 8, "-$(CH_2)_1$" should read-- -$(CH_2)_l$--.
In column 21, line 62, CLAIM 8, "-$NR_a$," should read -- -$NR_a$;--.

Signed and Sealed this

Sixth Day of November, 2007

JON W. DUDAS
*Director of the United States Patent and Trademark Office*